United States Patent [19]
Batchelor et al.

[11] Patent Number: 5,998,427
[45] Date of Patent: *Dec. 7, 1999

[54] ANDROSTENONES

[75] Inventors: Kenneth William Batchelor; Stephen Vernon Frye, both of Durham, N.C.

[73] Assignee: Glaxo Wellcome Inc., Research Triangle Park, N.C.

[*] Notice: This patent is subject to a terminal disclaimer.

[21] Appl. No.: 09/078,468

[22] Filed: May 14, 1998

Related U.S. Application Data

[60] Division of application No. 08/617,859, filed as application No. PCT/US94/10479, Sep. 16, 1994, Pat. No. 5,817,818, which is a continuation-in-part of application No. 08/123,280, Sep. 17, 1993, abandoned, and a continuation-in-part of application No. 08/136,515, Dec. 10, 1993, abandoned.

[51] Int. Cl.⁶ .......................... A61K 31/58; C07D 221/18
[52] U.S. Cl. ............................................. 514/284; 546/77
[58] Field of Search ................................ 514/284; 546/77

[56] References Cited

U.S. PATENT DOCUMENTS

| | | | |
|---|---|---|---|
| 4,377,584 | 3/1983 | Rasmusson et al. | 424/258 |
| 4,760,071 | 7/1988 | Rasmusson et al. | 514/284 |
| 5,017,568 | 5/1991 | Holt et al. | 514/173 |
| 5,084,574 | 1/1992 | Bhattacharya et al. | 546/77 |
| 5,098,908 | 3/1992 | Steinberg et al. | 540/966 |
| 5,215,894 | 6/1993 | Arison et al. | 435/53 |
| 5,565,467 | 10/1996 | Batchelor et al. | 514/284 |
| 5,693,810 | 12/1997 | Rasmusson et al. | 546/77 |
| 5,846,976 | 12/1998 | Batchelor et al. | 514/284 |

FOREIGN PATENT DOCUMENTS

| | | |
|---|---|---|
| 004949 A1 | 4/1979 | European Pat. Off. . |
| 271219 A1 | 11/1987 | European Pat. Off. . |
| 271220 A1 | 11/1987 | European Pat. Off. . |
| 277002 A2 | 1/1988 | European Pat. Off. . |
| 285383 A2 | 3/1988 | European Pat. Off. . |
| 414490 A2 | 8/1990 | European Pat. Off. . |
| 414491 A2 | 8/1990 | European Pat. Off. . |
| 428366 A2 | 11/1990 | European Pat. Off. . |
| 462662 A2 | 6/1991 | European Pat. Off. . |
| 462664 A2 | 6/1991 | European Pat. Off. . |
| 484094 A2 | 10/1991 | European Pat. Off. . |
| 538192 A1 | 8/1992 | European Pat. Off. . |
| 547687 A2 | 6/1993 | European Pat. Off. . |
| 5170789 | 12/1991 | Japan . |
| WO92/16213 | 3/1992 | WIPO . |
| WO92/16233 | 3/1992 | WIPO . |
| WO92/18132 | 4/1992 | WIPO . |
| WO93/23038 | 11/1993 | WIPO . |
| WO93/23039 | 11/1993 | WIPO . |
| WO93/23040 | 11/1993 | WIPO . |
| WO93/23041 | 11/1993 | WIPO . |
| WO93/23042 | 11/1993 | WIPO . |
| WO93/23048 | 11/1993 | WIPO . |
| WO93/23050 | 11/1993 | WIPO . |
| WO93/23051 | 11/1993 | WIPO . |
| WO93/23053 | 11/1993 | WIPO . |
| WO93/23419 | 11/1993 | WIPO . |
| WO93/23420 | 11/1993 | WIPO . |
| WO94/07861 | 4/1994 | WIPO . |

OTHER PUBLICATIONS

McGinley, et al., *New England Journal of Medicine*, 300, 1979, pp. 1233–1237.
Robaire, et al., *J. Steroid Biochem.*, 8, 1977, pp. 307–310.
Petrow, et al., *Steroids*, 38, 1981, p. 121.
Liang, et al., *J. Steroid Biochem.*, 19, 1983, pp. 385–390.
Holt, et al., *J. Med. Chem.*, 33, 1990, 937–942 "Steroidal A Ring Aryl Carboxylic Acids: A New Class of Steroid 5–Reductase Inhibitors".
Stoner, et al., *J. Steroid Biochem. Molec. Biol.*, vol. 37, 1990, pp. 375–378.
Russell, D.W., et al., *J. Clin. Invest.*, 89, 1992, p. 293.
Russell, D.W., et al., *Nature*, 354, 1991, p. 159.
Russell, D.W., et al., *New England J. of Med.*, 327, 1992, p. 1216.
Russell, D.W., et al., *J. Clin. Invest.*, 90, 1992, p. 799.
Brooks, et al., *Steroids*, 47, 1986, p. 1, "5α–Reductase Inhibitory and Anti–Androgenic Activities of Some 4–Azasteroids in the Rat".
Rasmusson, et al., *J. Med. Chem.*, 29, 1986, pp. 2298–2315, "Steroids: Structure–Activity Relationships for Inhibition of 5α–Reductase and Androgen Receptor Binding".

(List continued on next page.)

*Primary Examiner*—John Kight
*Assistant Examiner*—Charanjit S. Aulakh
*Attorney, Agent, or Firm*—Robert H. Brink

[57] ABSTRACT

The present invention relates to compounds of formula (I), wherein carbons 1 and 2 are joined by either a single or a double bond; $R^1$ is hydrogen or methyl; $R^2$ is hydrogen or methyl; $R^3$ is (B) wherein X, $R^6$, $R^7$ and $R^8$ are various groups, and pharmaceutically acceptable solvates thereof and their use in the treatment of androgen responsive and mediated diseases.

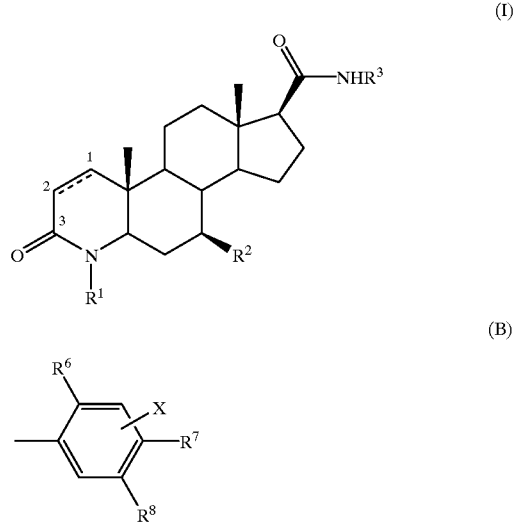

19 Claims, No Drawings

OTHER PUBLICATIONS

Rasmusson, et al., *J. of Med. Chem.*, 27, 1984, pp. 1690–1701, "Azasteroids a Inhibitors of Rat Prostatic 5α–Reductase".

Imperator, et al., *IG*, 1986, 130–133, "Inherited 5'–Reductase Deficiency in Man".

Jones, et al., *British J. of Urology*, 66, 1990, pp. 506–508, "Origin and Structure of Benign Prostatic Hyperplasia".

Blakitnyi, et al., *J. of Organic Chem.*, vol. 10, No. 3, 1974, pp. 512–516, "Synthesis of the Analogs of 3–p–Menthanol With a Fluorinated Methyl Group."

Reetz, et al., *Angew. Chem. Int. Ed. Engl.*, vol. 19, No. 11, 1980, pp. 900–901, "Geminal Dialkylation of Ketones with Grignard Compounds and Methyltitanium (IV) Chlorides."

Davies, H.W., et al., *Tetrahedron Letters*, vol. 30, No. 38, 1989, pp. 5057–5060, "Stereoselective Cyclopropanations with Vinylcarbenoids."

Baum, et al., *Synthetic Communications*, vol. 17, No. 14, 1987, pp. 1709–1716, "Diazotransfer Reactions with p–Acetamidobenzenesulfonyl Azide."

He, et al., *J. Med. Chem.*, 36, 1993, pp. 1188–1193, Synthesis and Biological Evaluation of 1–[1–(2–Benzo[b]thienyl)cyclohexyl]piperidine Homologues at Dopamine–Uptake and Phencyclidine– and σ–Binding Sites.

ANDROSTENONES

This application is a divisional of application Ser. No. 08/617,859 filed Mar. 14, 1996 and now U.S. Pat. No. 5,817,818, which is a 35 U.S.C. § 371 of PCT US94/10479 filed Sep. 16, 1994, which is a continuation in part of U.S. Ser. No. 08/123,280, filed Sep. 17, 1993 now abandoned and U.S. Ser. No. 08/136,515, filed Dec. 10, 1993, now abandoned.

The present invention relates to certain substituted 17β-anilide-4-aza-5α-androstan-3-ones, in particular as surprisingly potent and selective dual inhibitors of type 1 and 2 human 5α-reductase.

BACKGROUND OF THE INVENTION

Androgens are responsible for many physiological functions in both males and females. Androgen action is mediated by specific intracellular hormone receptors expressed in androgen responsive cells. Testosterone, the major circulating androgen, is secreted by Leydig cells of the testes under the stimulation of pituitary-derived luteinizing hormone (LH). However, reduction of the 4, 5 double bond of testosterone to dihydrotestosterone (DHT) is required in some target tissues, such as prostate and skin, for androgen action. Steroid 5α-reductases in target tissues catalyze conversion of testosterone to DHT in an NADPH dependent fashion as shown in Scheme A.

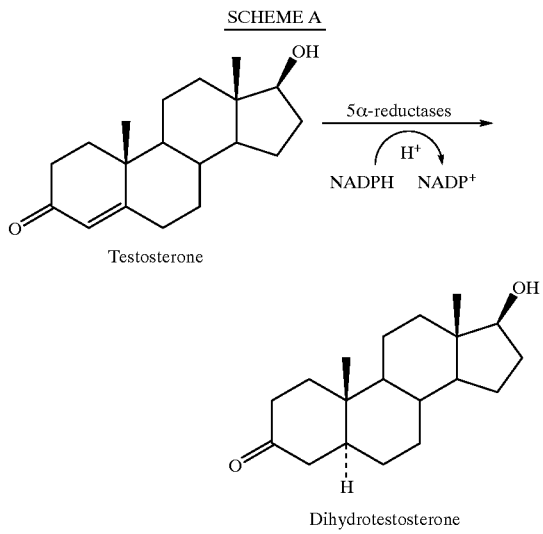

The requirement for DHT to act as an agonist in these target tissues has been highlighted by studies of steroid 5α-reductase deficient individuals who have vestigial prostate glands and do not suffer from acne vulgaris or male pattern baldness (see McGinley, J. et al., *The New England J. of Medicine,* 300, 1233 (1979)). Thus, inhibition of the conversion of testosterone to DHT in these target tissues is anticipated to be useful in the treatment of a variety of androgen responsive diseases, e.g., benign prostatic hyperplasia, prostate cancer, acne, male pattern baldness and hirsutism.

Additionally, it has recently been discovered that two isozymes of 5α-reductase exist in humans which differ in their tissue distribution, affinity for testosterone, pH profile and sensitivity to inhibitors (see Russell, D. W. et al.,*J. Clin. Invest.,* 89, 293 (1992); Russell, D. W. et al., *Nature,* 354, 159 (1991)). The steroid 5α-reductase deficient individuals studied by Imperato-McGinley are deficient in the type 2, 5α-reductase enzyme (Russell, D. W. et al.,*J. Clin. Invest.,* 90, 799 (1992); Russell, D. W. et al.,*New England J. Med.,* 327, 1216 (1992)), which is the predominant isozyme present in the prostate, while the type 1 isozyme is predominant in the skin. The relative value of isozyme specific and dual inhibitors of the two isozymes of 5α-reductase will depend upon the type of disease treated (benign prostatic hyperplasia, prostate cancer, acne, male pattern baldness or hirsutism) as well as the stage of the disease (prevention versus treatment) and the anticipated side-effects in the intended patients (for example treatment of acne vulgaris in pubescent males).

Because of their valuable therapeutic potential, testosterone 5α-reductase inhibitors [hereinafter "5α-reductase inhibitors"] have been the subject of active research worldwide. For example, see: Hsia, S. and Voight, W., *J. Invest. Derm.,* 62, 224 (1973); Robaire, B. et al., *J. Steroid Biochem.,* 8, 307 (1977); Petrow, V. et al, *Steroids,* 38, 121 (1981); Liang, T. et al.,*J. Steroid Biochem.,* 19, 385 (1983); Holt, D. et al.,*J. Med. Chem.,* 33, 937 (1990); U.S. Pat. Nos. 4,377,584, 4,760,071 and 5,017,568. Two particularly promising 5α-reductase inhibitors are MK-906 (Merck), known by the generic name, finasteride, and marketed under the trademark, Proscar; and SKF-105657 (SmithKline Beecham), shown in Scheme B.

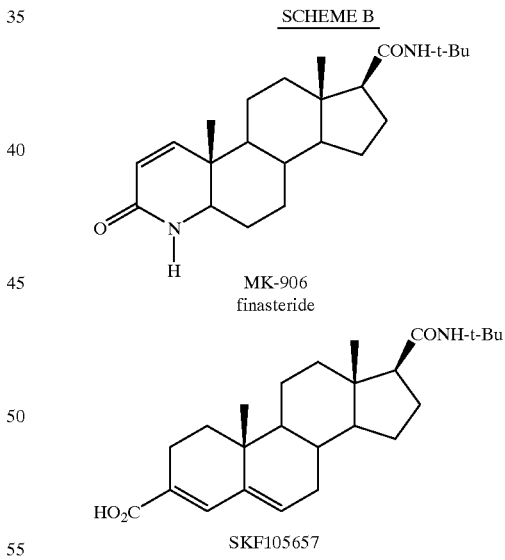

The potent inhibition of bovine adrenal and porcine granulosa cell 3β-hydroxy-Δ$^5$-steroid dehydrogenase/3-keto-Δ$^5$-steroid isomerase (3BHSD) by the 4-azasteroid derivative, 4-MA, shown in Scheme C and not by the drug finasteride

SCHEME C

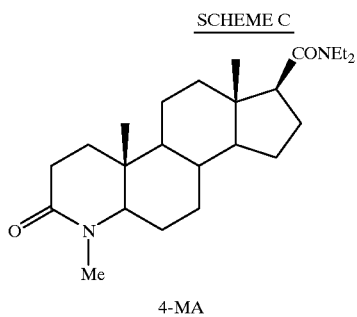

4-MA (Tan, C. H.; Fong, C. Y.; Chan, W. K. *Biochem. Biophys. Res. Comm.*, 144, 166 (1987) and Brandt, M.; Levy, M. A. *Biochemistry*, 28, 140 (1989)) along with the critical role of 3BHSD in steroid biosynthesis (Potts, G. O. et al., *Steroids*, 32, 257 (1978)), suggests that optimal inhibitors of type 1 and 2 5α-reductase should also be selective versus human adrenal 3BHSD. The importance of selectivity in 5α-reductase inhibitors has been emphasized by reports of hepatotoxicity in certain 4-azasteroids such as 4-MA (McConnell, J. D. *The Prostate Suppl.*, 3, 49 (1990) and Rasmusson, G. H. et al. *J. Med. Chem.*, 27, 1690 (1984)).

SUMMARY OF THE INVENTION

One aspect of the present invention provides compounds of formula (I),

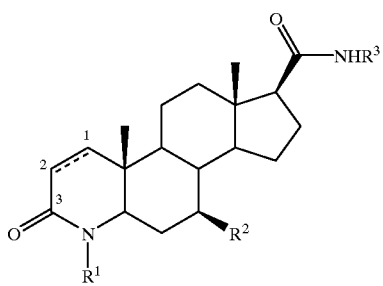

(I)

wherein
carbons 1 and 2 are joined by either a single or a double bond;
$R^1$ is hydrogen or methyl;
$R^2$ is hydrogen or methyl;
$R^3$ is (A)

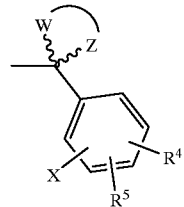

(A)

wherein,
$R^4$ and $R^5$ are independently hydrogen, lower alkyl, lower alkoxy, trifluoromethyl, cyano, halogen, phenyl (optionally substituted with one or more halogens), or when $R^4$ and $R^5$ are on adjacent carbons, taken together form a fused 5, 6 or 7 member ring optionally containing one or more oxygen or sulfur atoms;

W and Z are methylene groups which taken together with the carbon to which they are attached form a saturated, 3 to 12 member ring system optionally:
1) substituted independently with one or more lower alkyl groups,
2) containing an oxygen or sulfur atom,
3) two said methylene groups of said 3 to 12 member ring are joined with a ($C_{1-6}$) alkylene group to form a bicyclic ring system, and X is hydrogen or halogen;
or (B)

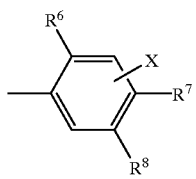

(B)

wherein,
$R^6$ is trifluoromethyl, phenyl optionally substituted with one or more halogens or branched ($C_{4-7}$) alkyl groups, or branched ($C_{4-7}$) alkyl;
either of $R^7$ or $R^8$ is trifluoromethyl, halogen, phenyl optionally substituted with one or more halogens or branched ($C_{4-7}$)alkyl groups, or branched ($C_{4-7}$) alkyl, while the other is hydrogen or halogen; and
X is hydrogen or halogen,
and pharmaceutically acceptable solvates thereof.
Other aspects of the invention are:
1. A method of inhibiting testosterone-5α-reductases comprising contacting testosterone-5α-reductases with a compound of formula (I).
2. A method of treatment of androgen responsive or mediated disease comprising administering an effective amount of a compound of formula (I) to a patient in need of such treatment.
3. Pharmaceutical formulations containing a compound of formula (I) as an active ingredient.
4. A method of treatment of androgen responsive or mediated disease comprising administering an effective amount of a compound of formula (I) to a patient in need of such treatment in combination with an antiandrogen such as flutamide.
5. A method of treatment of benign prostatic hyperplasia comprising administering an effective amount of a compound of formula (I) to a patient in need of such treatment in combination with an alpha 1 adrenergic receptor blocker (e.g. terazosin).
6. A method of treatment of benign prostatic hyperplasia comprising administering an effective amount of a compound of formula (I) to a patient in need of such treatment in combination with an anti-estrogen.
7. Certain chemical intermediates used in the preparation of compounds of formula

DETAILED DESCRIPTION OF THE INVENTION

Compounds

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of formula (I) are within the scope of the invention.

It will also be appreciated by those skilled in organic chemistry that many organic compounds can exist in more than one crystalline form. For example, crystalline form may vary from solvate to solvate. Thus, all crystalline forms of the compounds of formula (I) or the pharmaceutically acceptable solvates thereof are within the scope of the present invention.

As used herein the term "lower" in relation to alkyl and alkoxy means 1 to 6 carbons, especially 1 to 4, straight or branched. As used herein the term "branched ($C_{4-7}$) alkyl" means 3–6 carbons attached via a quaternary carbon, e.g., t-butyl, t-amyl, etc. The term "halogen" means fluoro, chloro, bromo, and iodo moieties.

Examples of the ring systems formed by W and Z include, but are not limited to: cyclopropyl, cyclobutyl, cyclopentyl, cyclohexyl, cycloheptyl, cyclooctyl, cyclodo-decyl, etc.; norbornyl, bicyclo[3.3.1]nonyl, tetrahydrofuryl, tetrahydropyranyl, or tetrahydrothiopyranyl. Ring systems of 3 to 8 members are preferred.

Examples of bicyclic ring systems formed when one of the W methylene groups is joined to one of the Z methylene groups by a ($C_{1-6}$) alkylene group include, but are not limited to:

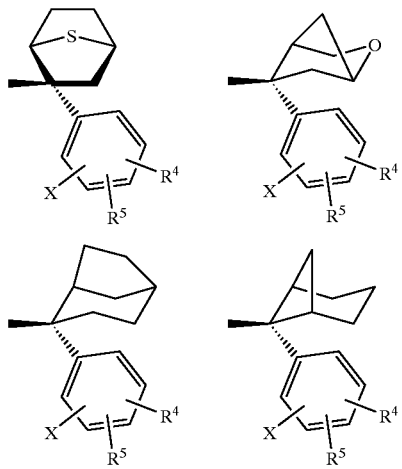

Examples of fused 5, 6 or 7 member rings formed by $R^4$ and $R^5$ include but are not limited to:

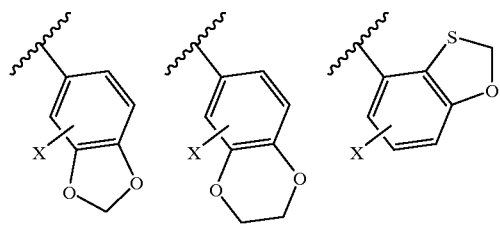

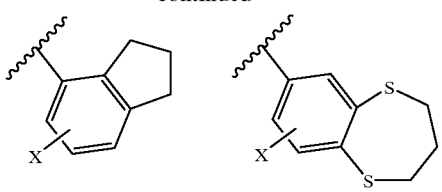

It will be appreciated by those skilled in the art of organic chemistry that the "quaternary carbon" of substituent (A), i.e., the carbon upon which —NH—, the phenyl group, W and Z are attached, may be asymmetric. This asymmetry about the quaternary carbon gives rise to a pair of stereoisomers (see March, J., Advanced Organic Chemistry, 3$^{rd}$ Ed., Chap. 4, "Stereochemistry", John Wiley and Sons, New York (1985)). Further, when W and Z are substituted with alkyl groups or are joined with an alkylene group, other asymmetric carbons may be established also resulting in other pairs of stereoisomers. All stereoisomers of the novel compounds taught herein are within the scope of the present invention.

As used herein the rippled lines representing single bonds connecting the quaternary carbon to W and to Z indicate that these two bonds can be of either an α or β relationship with respect to the quaternary carbon. The term "α" means the bond and corresponding substituent extends below the plane of the page while the term "β" means the bond and corresponding substituent extends above the plane of the page and is depicted herein by a solid wedge shape bond. The use of these terms is consistent with standard chemical terminology.

In a particular group of the compounds of formula (I), X is hydrogen. In another particular group of the compounds of formula (I), $R^2$ is hydrogen. In yet another group of the compounds of formula (I), $R^6$ is trifluoromethyl, phenyl optionally substituted with one or more halogens, or branched ($C_{4-7}$) alkyl; and either of $R^7$ or $R^8$ is trifluoromethyl, halogen, phenyl optionally substituted with one or more halogens, or branched ($C_{4-7}$) alkyl, while the other is hydrogen or halogen. In another particular group of the compounds of formula (1), carbons 1 and 2 are joined by a double bond.

A particular group of the compounds of formula (I) are the compounds of formula (IA)

(IA)

wherein
carbons 1 and 2 are joined by either a single or a double bond;
$R^1$ is hydrogen or methyl;
$R^4$ and $R^5$ are independently hydrogen, lower alkyl, lower alkoxy, trifluoromethyl, cyano, halogen, phenyl (optionally substituted with one or more halogens), or when $R^4$ and $R^5$ are on adjacent carbons, taken together form a fused 5, 6 or 7 member ring optionally containing one or more oxygen or sulfur atoms;

W and Z are methylene groups which taken together with the carbon to which they are attached form a saturated, 3 to 12 member ring system optionally:
 1) substituted with one or more lower alkyl groups,
 2) containing an oxygen or sulfur atom, and
 3) two said methylene groups of said 3 to 12 member ring are joined with a ($C_{1-6}$) alkylene group to form a bicyclic ring system; and X is hydrogen or halogen.

In a particular group of the compounds of formula (IA);
$R^4$ and $R^5$ are independently hydrogen, lower alkyl, lower alkoxy, trifluoromethyl, cyano, halogen, or phenyl (optionally substituted with one or more halogens); and
X is hydrogen;

Compounds of formula (IA) wherein at least one of X, $R^4$ and $R^5$ is other than hydrogen are preferred. Substituents in the para (4-) position of the phenyl ring are especially preferred.

In a particular group of the compounds of formula (IA) at least one of $R^4$ and $R^5$ is lower alkyl, lower alkoxy, trifluoromethyl, halogen or phenyl, especially branched alkyl, e.g., t-butyl, trifluoromethyl, or halogen.

In four other particular groups of the compounds of formula (IA):
 1) W and Z are methylene groups which taken together with the carbon to which they are attached form a saturated, 3 to 12 member ring system containing only carbon atoms and which may be substituted independently with one or more lower alkyl groups; or
 2) W and Z are methylene groups which taken together with the carbon to which they are attached form a saturated, 3 to 12 member ring system containing an oxygen or sulfur atom and which may be substituted independently with one or more lower alkyl groups; or
 3) W and Z are methylene groups which taken together with the carbon to which they are attached form a saturated, 3 to 12 member ring system containing only carbon atoms and which may be substituted independently with one or more lower alkyl groups and two said methylene groups are joined with a ($C_{1-6}$) alkylene group to form a bicyclic ring system; or
 4) W and Z are methylene groups which taken together with the carbon to which they are attached form a saturated, 3 to 12 member ring system containing an oxygen or sulfur atom and which may be substituted independently with one or more lower alkyl groups and two said methylene groups are joined with a ($C_{1-6}$) alkylene group to form a bicyclic ring system.

Another particular group of the compounds of formula (I) are the compounds of formula (IB);

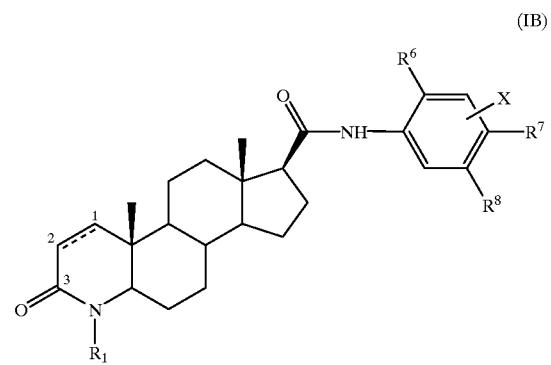

wherein
carbons 1 and 2 are joined by either a single or a double bond;
$R^1$ is hydrogen or methyl;
$R^6$ is trifluoromethyl, phenyl optionally substituted with one or more halogens, or branched ($C_{4-7}$) alkyl;
either of $R^7$ or $R^8$ is trifluoromethyl, halogen, phenyl optionally substituted with one or more halogens, or branched ($C_{4-7}$) alkyl, while the other is hydrogen or halogen;
X is hydrogen or halogen.

In a particular group of the compounds of formula (IB) when $R^7$ or $R^8$ is branched ($C_{4-7}$) alkyl and X is hydrogen, $R^6$ is trifluoromethyl or phenyl optionally substituted with one or more halogens.

In another particular group of the compounds of formula (IB);
$R^6$ is trifluoromethyl or branched ($C_{4-7}$) alkyl;
either of $R^7$ or $R^8$ is trifluoromethyl, halogen, or phenyl substituted with one or more halogens, while the other is hydrogen or halogen.

In another particular group of the compounds of formula (IB);
$R^6$ is trifluoromethyl or branched ($C_{4-7}$) alkyl;
either of $R^7$ or $R^8$ is trifluoromethyl while the other is hydrogen;
X is hydrogen.

In another particular group of the compounds of formula (IB) $R^6$ and $R^8$ are independently trifluoromethyl or t-butyl, while $R^7$ and X are hydrogen.

Specific compounds of formula (I) are:

| Compound/<br>Example<br>Number | Compound<br>Name |
|---|---|
| 1. | 17β-N-1-(4-Chlorophenyl)cyclopentylcarbamoyl-4-aza-5α-androstan-3-one |
| 2. | 17β-N-1-(4-Chlorophenyl)cyclopentylcarbamoyl-4-methyl-4-aza-5α-androstan-3-one |
| 3. | 17β-N-1-(4-Chlorophenyl)cyclopentylcarbamoyl-4-aza-5α-androst-1-en-3-one |
| 4. | 17β-N-1-(4-t-Butylphenyl)cyclopentylcarbamoyl-4-aza-5α-androst-1-en-3-one |
| 5. | 17β-N-1-(4-t-Butylphenyl)cyclohexylcarbamoyl-4-aza-5α-androst-1-en-3-one |
| 6. | 17β-N-1-(4-Chlorophenyl)cyclohexylcarbamoyl-4-aza-5α-androst-1-en-3-one |
| 7. | 17β-N-1-(4-Trifluoromethylphenyl)cyclopentylcarbamoyl-4-aza-5α-androst-1-en-3-one |

-continued

| Compound/ Example Number | Compound Name |
|---|---|
| 8. | 17β-N-1-(4-Methoxyphenyl)cyclopentylcarbamoyl-4-aza-5α-androst-1-en-3-one |
| 9. | 17β-N-1-(4-Fluorophenyl)cyclopentylcarbamoyl-4-aza-5α-androst-1-en-3-one |
| 10. | 17β-N-1-(4-Fluorophenyl)cyclohexylcarbamoyl-4-aza-5α-androst-1-en-3-one |
| 11. | 17β-N-1-(4-Methoxyphenyl)cyclohexylcarbamoyl-4-aza-5α-androst-1-en-3-one |
| 12. | 17β-N-1-(3,4-Methylenedioxyphenyl)cyclohexylcarbamoyl-4-aza-5α-androst-1-en-3-one |
| 13. | 17β-N-1-(4-t-Butylphenyl)cycloheptylcarbamoyl-4-aza-5α-androst-1-en-3-one |
| 14. | 17β-N-4-(4-t-Butylphenyl)tetrahydropyranylcarbamoyl-4-aza-5α-androst-1-en-3-one |
| 15. | 17β-N-1-(2,4-Dichlorophenyl)cyclopropylcarbamoyl-4-aza-5α-androst-1-en-3-one |
| 16. | 17β-N-1-(4-Trifluoromethylphenyl)-2,2-diethylcyclopropylcarbamoyl-4-aza-5α-androst-1-en-3-one |
| 17. | 17β-N-1-(4-t-Butylphenyl)-4,4-dimethylcyclohexylcarbamoyl-4-aza-5α-androst-1-en-3-one |
| 18. | 17β-N-1-(4-t-Butylphenyl)-4-t-Butylcyclohexylcarbamoyl-4-aza-5α-androst-1-en-3-one |
| 19. | 17β-N-1-(3-Trifluoromethylphenyl)cyclopentylcarbamoyl-4-aza-5α-androst-1-en-3-one |
| 20. | 17β-N-4-(4-t-Butylphenyl)tetrahydrothiopyranylcarbamoyl-4-aza-5α-androst-1-en-3-one |
| 21. | 17β-N-1-(4-Biphenyl)-2,2-diethylcyclopropylcarbamoyl-4-aza-5α-androstan-1-en-3-one |
| 22. | 17β-N-(2,5-bis(Trifluoromethyl))phenylcarbamoyl-4-aza-5α-androstan-3-one |
| 23. | 17β-N-(2,5-bis(Trifluoromethyl))phenylcarbamoyl-4-methyl-4-aza-5α-androstan-3-one |
| 24. | 17β-N-(2-t-Butyl-5-trifluoromethyl)phenylcarbamoyl-4-aza-5α-androst-1-en-3-one |
| 25. | 17β-N-(2-t-Butyl-5-trifluoromethyl)phenylcarbamoyl-4-aza-5α-androst-3-one |
| 26. | 17β-N-(2-t-Butyl-5-trifluoromethyl)phenylcarbamoyl-4-methyl-4-aza-5α-androstan-3-one |
| 27. | 17β-N-(2,5-Di-t-butyl)phenylcarbamoyl-4-aza-5α-androst-1-en-3-one |
| 28. | 17β-N-(2,5-Di-t-butyl)phenylcarbamoyl-4-aza-5α-androstan-3-one |
| 29. | 17β-N-(2,5-Di-t-butyl)phenylcarbamoyl-4-methyl-4-aza-5α-androstan-3-one |
| 30. | 17β-N-(2,5-bis(Trifluoromethyl)phenylcarbamoyl-4-aza-7β-methyl-5α-androst-1-en-3-one |
| 31. | 17β-N-(2-t-Butyl-5-trifluoromethyl)phenylcarbamoyl-4-aza-7β-methyl-5α-androst-1-en-3-one |
| 32. | 17β-N-1-(4-Chlorophenyl)cyclopentylcarbamoyl-4-aza-7β-methyl-5α-androst-1-en-3-one |
| 33. | 17β-N-9-(4-t-Butylphenyl)bicyclo[3.3.1]nonylcarbamoyl-4-aza-5αandrost-1-en-3-one |

A particular specific compound of formula (I) is:

17β-N-1-(4-Chlorophenyl)cyclopentylcarbamoyl-4-aza-5α-androst-1-en-3-one

Specific intermediate compounds of formulas (III), (IV) and (IVa) are:

17β-N-1-(4-chlorophenyl)cyclopentylcarbamoyl-androst-4-en-3-one;

17β-N-1-(4-chlorophenyl)cyclopentylcarbamoyl-5-oxo-A-nor-3,5-secoandrostan-3-oic acid; and 17β-N-1-(4-chlorophenyl)cyclopentylcarbamoyl-4-aza-androst-5-en-3-one.

Preparation of Compounds

The compounds of the present invention may be prepared by the methods taught in U.S. Pat. No. 4,377,584 (hereinafter, "'584") and U.S. Pat. No. 4,760,071 (hereinafter, "'071") both incorporated herein by reference. For example, compounds of formula (I) wherein carbons 1 and 2 are joined by a single bond may be prepared by the procedure shown in Scheme I.

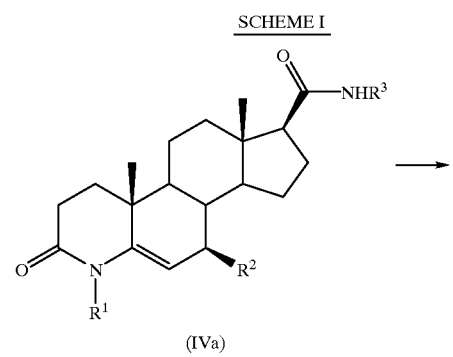

SCHEME I (IVa)

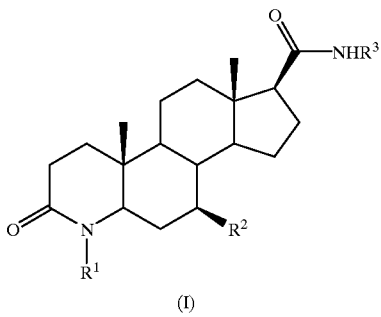

In Scheme I, the 4-aza-androst-5-en-3-one compound of formula (IVa) is converted to the corresponding 4-aza-5α-androstan-3-one of formula (I) by hydrogenation. For example, the hydrogenation may be carried out in acetic acid at 60 to 70° C. and 40–60 psi hydrogen pressure in the presence of catalytic platinum oxide.

Compounds of formula (IVa) may be prepared by the procedure of Scheme IA:

The compounds of formula (IIa) wherein $R^3$ is (A) i.e., cycloalkylbenzylamines, are prepared by Curtius rearrangement of the corresponding acid, where available, or by the method of He, X. et al., *J. Med. Chem.,* 36, 1188 (1993), i.e. by reacting the corresponding cycloalkanone with the appropriate aryl Grignard reagent followed by conversion of the resulting alcohol to the amine by treatment with sodium azide and trifluoroacetic acid followed by reduction of the azide with lithium aluminum hydride. Substituted cyclopropylbenzylamines of formula (IIa) are prepared by rhodium catalyzed insertion of the appropriate aryl-α-diazo-ester (prepared by the method of Baum, J. S. et al., *Synthetic Comm.,* 17, 1709 (1987)) into the appropriate olefin (as described by Davies, H. W. et al., *Tetrahedron Lett.,* 30, 5057 (1989)) followed by saponification of the ester and Curtius rearrangement of the acid to give the desired amine. The compounds of formula (IIa) wherein $R^3$ is (B), i.e., substituted anilines, are commercially available or conveniently prepared by methods known in the art (see Blakitnyi et al, *J. Org. Chem. USSR* (English translation),.10, 512 (1974) abstracted in *CA* 80 (25): 14623f and Reetz, M. T. et al., *Angew. Chem. Int. Ed. Engl.,* 19, 900 and 901 (1980)).

In Step 2, the compound of formula (III) is converted to the 5-oxo-A-nor-3,5-secoandrostan-3-oic acid derivative of

SCHEME IA

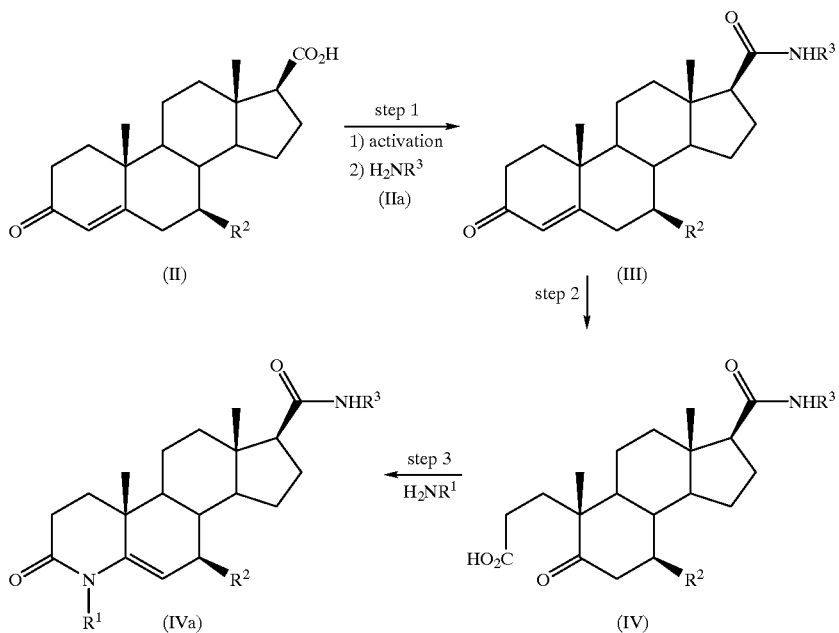

In Step 1 of Scheme IA, 3-oxo-4-androstene-17β-carboxylic acid (II) is converted to the corresponding amide of formula (III). This may be accomplished by activation of the acid and reaction with a compound of formula (IIa). For example, the reaction sequence can be conversion of a compound of formula (II) to the corresponding acid halide by treatment with a halogenating agent such as oxalyl chloride or thionyl chloride in an aprotic solvent such as toluene, methylene chloride or tetrahydrofuran at −5 to 10° C. in the presence of a base such as pyridine. The intermediate acid halide, e.g., an acid chloride, may be reacted with an amine of formula (IIa) (wherein the substituents are as defined for formula (I)), optionally in the presence of a catalyst such as 4-N,N-dimethylaminopyridine, at 25 to 70° C. in an aprotic solvent such as tetrahydrofuran to give the amide of formula (III).

formula (IV) by oxidation, e.g. by treatment with aqueous sodium permanganate and sodium periodate under basic conditions at reflux in t-butanol.

In Step 3, the compound of formula (IV) is converted to the corresponding compound of formula (IVa) by treatment with a compound of the formula $NH_2R^1$, e.g., ammonia ($R^1$=H) or methylamine ($R^1$=methyl), at elevated temperatures in a protic or aprotic solvent, e.g., at reflux in ethylene glycol.

Compounds of formula (I) may also be prepared by interconversion from other compounds of formula (I). For example, the process of Scheme IB may be used to prepare a compound of formula (I) where there is a double bond between carbons 1 and 2, and where $R^1$ is hydrogen, i.e., the compound of formula (Ib) from the corresponding compound of formula (I), i.e., the compound of formula (Ia).

SCHEME IB

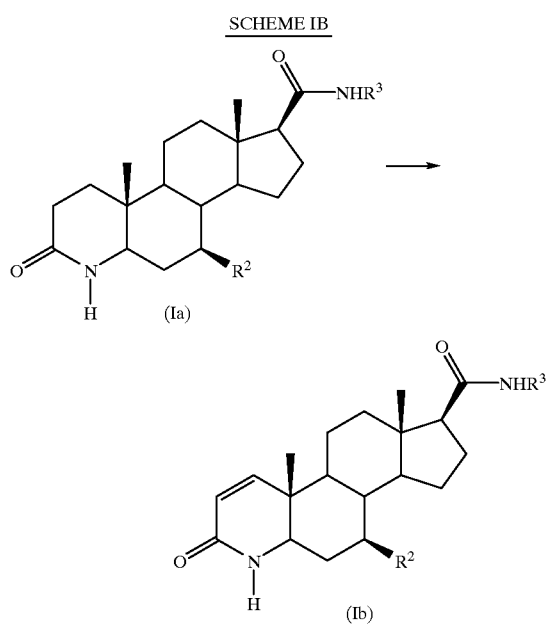

In Scheme IB, a compound of formula (Ia) is dehydrogenated to give the corresponding 4-aza-5α-androst-1-en-3-one of formula (Ib) by treatment with a dehydrogenating system, e.g. 2,3-dichloro-5,6-dicyano-1,4-benzoquinone (DDQ) and bis(tri-methylsilyl)trifluoroacetamide in dry dioxane at room temperature for 2–5 hrs followed by heating at reflux for 10–20 hrs (see Bhattacharya, A. et al., J. Am. Chem. Soc., 110, 3318 (1988).

SCHEME II

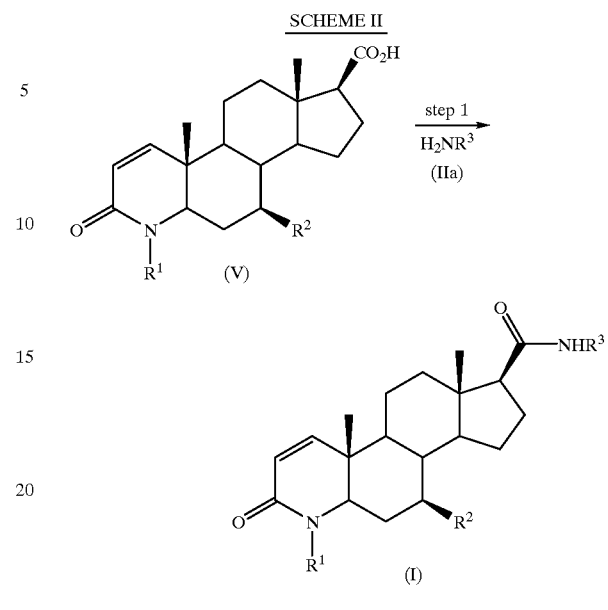

Alternatively, in Scheme II compounds of formula (I), wherein carbon 1 and 2 are joined by a double bond, may be prepared from 3-oxo-4-aza-5α-androst-1-ene-17β-carboxylic acids of formula (V) by reaction with a compound of formula (IIa) as described in Scheme IA, step 1. Compounds of formula (V) wherein $R^2$ is hydrogen may be prepared by the method of Rasmusson, G. H. et al., J. Med. Chem., 29, 2298 (1986). The compounds of formula (V) wherein $R^2$ is methyl may be prepared according to Scheme IIa.

SCHEME IIa

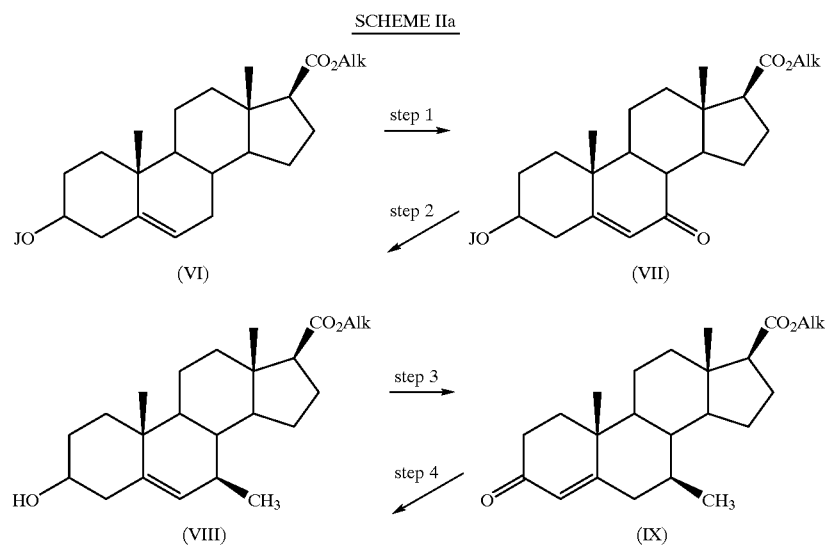

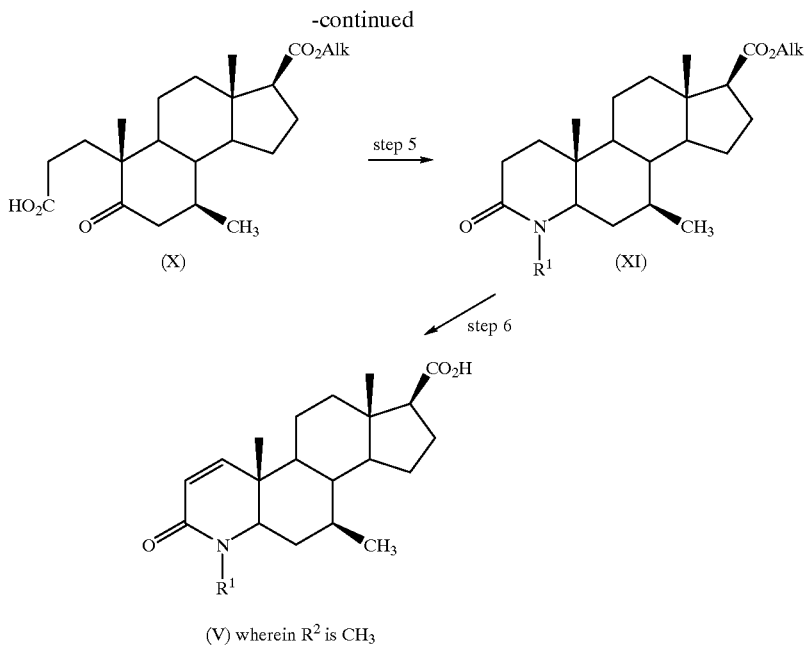

(V) wherein $R^2$ is $CH_3$

In Step 1, a compound of formula (VI), wherein JO is a protected hydroxy group, e.g., a triisopropylsilyloxy group, and $CO_2Alk$ is a carboxylic acid ester group, e.g., a methyl ester, is reacted with a strong, heavy metal oxidizing complex, e.g., chromic acid/3,5-dimethyl pyrazole in an aprotic solvent, e.g., dichloromethane, to yield the corresponding compound of formula (VII). Compounds of formula (VI) may be prepared from a 3β-hydroxyetienic acid ester (J. Med. Chem. 27, 1690) by the method taught in PCT patent application WO 94/14833. For example, 3β-hydroxyetienic acid methyl ester may be reacted with a hydroxy group protecting reagent such as triisopropylsilylchloride in the presence of a base, e.g., imidazole in an aprotic solvent, e.g., dimethyl formamide or dichloromethane, at moderate temperatures ranging from 25 to 55° C.

In Step 2, the 7-oxo moiety of the compound of formula (VII) is converted to a corresponding alkyl group, e.g., methyl group, by treatment with a Wittig reagent followed by catalytic hydrogenation and deprotection of the 3-hydroxy group to yield the corresponding compound of formula (VIII). For example, the compound of formula (VII) may be reacted with methyl triphenylphosphonium iodide and n-butyl lithium in an aprotic solvent, such as tetrahydrofuran in the temperature range of about −5° to 10° C., e.g., at 0° C. to yield the corresponding 7-alkylidene derivative. The exocyclic double bond may then be reduced selectively by treatment with tris(triphenylphosphine) rhodium chloride under a hydrogen atmosphere to yield predominately the 7β-alkyl substituted compound. The protecting group on the 3-hydroxy is then removed to yield the compound of formula VIII. For example, if the protecting group is triisopropylsilyl, it may be removed by treatment with tetrabutyl-ammonium fluoride in tetrahydrofuran.

In Step 3, the 3-hydroxy group of the compound of formula (VIII) is oxidized to yield the corresponding 3-oxo moiety with migration of the double bond to yield the compound of formula (IX). For example, the oxidation may be accomplished with Jones' reagent in an alkyl ketone, such as acetone, at about room temperature.

In Step 4, the compound of formula (IX) is oxidized in an analogous manner to that described in Step 2 of Scheme IA to yield the corresponding 5-oxo-A-nor-3,5-secoandrostan-3-oic acid derivative of formula (X).

In Step 5, the compound of formula (X) is converted to the corresponding compound of formula (XI) in an analogous manner to that described in Scheme I.

In Step 6, the compound of formula (XI) is dehydrogenated in an analogous manner to that described in Scheme IB to yield the corresponding 4-aza-5α-androst-1-en-3-one derivative. The 17-carboxylic acid ester group is then converted by saponification to the corresponding 17-carboxylic acid group yielding the compound of formula (V). For example, the carboxylic acid ester group may be converted to the carboxylic group by treatment with a moderate to strong base in a protic or aprotic solvent, e.g., treatment with a metal hydroxide, such as lithium hydroxide, in dioxane/water at about room temperature.

Those skilled in the art will appreciate that at an earlier stage in the preparation of a compound of formula (I) or a solvate thereof it may have been necessary and/or desirable to protect one or more sensitive groups in the molecule to prevent undesirable side reactions.

The protecting groups used in the preparation of compounds of formula (I) may be used in a conventional manner. See for example Protective Groups in Organic Chemistry, Ed. J. F. W. McOmie, Plenum Press, London (1973) or Protective Groups in Organic Synthesis, Theodora Green, John Wiley and Sons, New York (1981).

Removal of any protecting groups present may be achieved by conventional procedures. An arylalkyl group such as benzyl, may be cleaved by hydrogenolysis in the presence of a catalyst, e.g., palladium on charcoal; an acyl group such as N-benzyloxycarbonyl may be removed by hydrolysis with, for example, hydrogen bromide in acetic acid or by reduction, for example by catalytic hydrogenation.

As will be appreciated, in any of the general processes described above it may be desirable or even necessary to protect any sensitive groups in the molecule as just described. Thus, a reaction step involving deprotection of a protected derivative of general formula (I) or a salt thereof may be carried out subsequent to any of the above described processes.

Thus, according to a further aspect of the invention, the following reactions may, if necessary and/or desired be carried out in any appropriate sequence subsequent to any of the general processes:
  (i) removal of any protecting groups; and
  (ii) conversion of a compound of formula (I) or a solvate thereof into a pharmaceutically acceptable solvate thereof.

As well as being employed as the last main step in the preparative sequence, the general methods indicated above for the preparation of the compounds of the invention may also be used for the introduction of the desired groups at an intermediate stage in the preparation of the required compound. It should therefore be appreciated that in such multi-stage processes, the sequence of reactions should be chosen in order that the reaction conditions do not affect groups present in the molecule which are desired in the final product.

The compounds of formula (I) and the intermediate compounds, (II)-(XI), shown in Schemes I and II may be purified by convenient methods of the art, e.g., chromatography or crystallization.

In vitro Assays
Steroid 5α-Reductases

Enzyme activities may be determined using microsomes derived from: 1) prostate tissue from benign prostatic hyperplasia (BPH) patients; 2) recombinant baculovirus infected SF9 cells that express human type 1 5α-reductase; or 3) recombinant baculovirus infected SF9 cells that express human type 2 5α-reductase. Microsomes were prepared by homogenization of the tissue or cells, followed by differential centrifugation of the homogenate. Microsome extracts were incubated with varying concentrations of [1,2,6,7-$^3$H]-testosterone, 1 mM NADPH, and varying amounts of the compounds of formula (I,) i.e. a test compound, in buffer containing a NADPH regenerating system capable of maintaining NADPH concentrations for a period of time within the range 0.5–240 minutes. Corresponding incubations were carried out with no test compound as a control study.

For type 1 $IC_{50}$ measurements, assay components except testosterone were preincubated for 10 minutes at pH 7.0, and following the addition of 100 nM testosterone the assays were allowed to proceed for 10–120 minutes. For type 2 $IC_{50}$ measurements, assay components except testosterone were preincubated for 20 minutes at pH 6.0, and following the addition of 8 nM testosterone the assays were allowed to proceed for 20–40 minutes. The percentage of conversion of testosterone to DHT in the presence of test compounds compared to the corresponding conversion in the control study was estimated using high performance liquid chromatography (HPLC) with radiochemical detection. The results of these assays appear as $IC_{50}$'s reported in Table 1.

3β-Hydroxy-$\Delta^5$-steroid Dehydrogenase/3-Keto-$\Delta^5$-steroid Isomerase

Enzyme activities are measured using microsomes derived from human adrenal tissues. Microsomes were prepared by homogenization of the tissue followed by differential centrifugation of the homogenate. Microsome extracts were incubated with varying concentrations of dehydroepiandrosterone (DHEA), 1 mM NAD$^+$, and varying amounts of the compounds of Formula (I), i.e. a test compound, in pH 7.5 buffer for a period of time within the range of 1 to 60 minutes. Corresponding incubations were carried out with no test compound as a control study. The percentage of conversion of DHEA to androstenedione in the presence of test compounds compared to the corresponding conversion in the control study was estimated using HPLC with radiochemical detection. The results of these assays appear as $K_i$'s reported in Table 1.

TABLE 1

5α-REDUCTASE (5AR) AND HUMAN ADRENAL 3β-HYDROXY-$\Delta^5$-STEROID DEHYDROGENASE/3-KETO-$\Delta^5$-STEROID ISOMERASE (3BHSD) in vitro INHIBITORY ACTIVITY

| Compound/ Example | $IC_{50}$ Human Type 1 5AR | $IC_{50}$ Human Type 2 5AR | $K_i$ Human Adrenal 3BHSD |
|---|---|---|---|
| 1 | +++ | ++++ | + |
| 2 | ++++ | ++++ | ++ |
| 3 | ++++ | ++++ | + |
| 4 | +++ | ++++ | + |
| 5 | +++ | ++++ | + |
| 6 | +++ | ++++ | + |
| 7 | +++ | ++++ | + |
| 8 | +++ | ++++ | + |
| 9 | +++ | ++++ | + |
| 10 | +++ | ++++ | + |
| 11 | +++ | ++++ | + |
| 12 | ++ | ++++ | ++ |
| 13 | +++ | ++++ | + |
| 14 | +++ | ++++ | + |
| 15 | +++ | ++++ | + |
| 16 | +++ | ++++ | + |
| 17 | ++++ | ++++ | + |
| 18 | +++ | ++++ | + |
| 19 | +++ | ++++ | + |
| 20 | ++++ | ++++ | + |
| 21 | ++++ | ++++ | + |
| 22 | +++ | ++++ | + |
| 23 | ++++ | ++++ | ++ |
| 24 | +++ | +++ | + |
| 25 | +++ | ++++ | + |
| 26 | ++++ | ++++ | ++ |
| 27 | +++ | ++++ | ++ |
| 28 | +++ | ++++ | + |
| 29 | ++++ | ++++ | ++ |
| 30 | +++ | +++ | + |
| 31 | +++ | +++ | + |
| 32 | +++ | ++++ | + |
| 33 | +++ | ++++ | + |

++++ <1 nM
+++ 1–10 nM
++ 10–1000 nM
+ >1000 nM

In vivo Evaluation of Steroid 5α-Reductase Inhibitor

The in vivo activity of steroid 5α-reductase inhibitors may be determined in a chronic rat model (Brooks, J. R. et al., Steroids, 47, 1 (1986)). The chronic model utilizes castrated male rats that are dosed daily with testosterone (20 μg/rat) subcutaneously and with test compound (0.01–10 mg/kg) or vehicle orally for 7 days. The animals are then sacrificed and their prostates weighed. Reduction in the size of testosterone-stimulated prostate weight demonstrated activity of the test compound. Known steroid 5α-reductase inhibitors were tested in parallel to ensure consistency of the assay method.

Utility

The steroid 5α-reductase inhibitors of the present invention are useful in the treatment of androgen responsive diseases, e.g., benign and malignant diseases of the prostate, especially benign prostatic hyperplasia, in a manner similar to that for other 5α-reductase inhibitors such as finasteride and SKF105657. For correlation of in vitro, rat in vivo, and human clinical data relating to an inhibitor of 5α-reductase, see Stoner, E. et al., J. Steroid Biochem. Molec. Biol., 37, 375 (1990); Brooks, J. R. et al., Steroids, 47, 1 (1986) and Rasmusson, G. H. et al., J. Med. Chem., 29, 2298 (1986)).

Compounds of this invention are also useful in the treatment of prostatitis, prostate cancer, androgen mediated diseases of the skin, such as acne, hirsutism and male pattern baldness. Other hormone related diseases, e.g., polycystic ovary disease, may also be treated with these compounds.

The amount of compound of formula (I) required to be effective as an 5α-reductase inhibitor will, of course, vary with the individual mammal being treated and is ultimately at the discretion of the medical or veterinary practitioner. The factors to be considered include the condition being treated, the route of administration, the nature of the formulation, the mammal's body weight, surface marea, age and general condition, and the particular compound to be administered. However, a suitable effective 5α-reductase inhibitory dose is in the range of about 0.001 to about 2 mg/kg body weight per day, preferably in the range of about 0.005 to about 1 mg/kg per day.

The total daily dose may be given as a single dose, multiple doses, e.g., two to six times per day, or by intravenous infusion for a selected duration. Dosages above or below the range cited above are within the scope of the present invention and may be administered to the individual patient if desired and necessary. For example, for a 75 kg mammal, a dose range would be about 0.4mg to about 75 mg per day, and a typical dose would be about 10 mg per day. If discrete multiple doses are indicated, treatment might typically be 2.5 mg of a compound of formula (I) given 4 times per day.

Formulations

Formulations of the present invention for medical use comprise an active compound, i.e., a compound of formula (I), together with an acceptable carrier thereof and optionally other therapeutically active ingredients. The carrier must be pharmaceutically acceptable in the sense of being compatible with the other ingredients of the formulation and not deleterious to the recipient thereof.

The present invention, therefore, further provides a pharmaceutical formulation comprising a compound of formula (I) together with a pharmaceutically acceptable carrier thereof.

The formulations include those suitable for oral, rectal, topical or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredient(s) may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Formulations suitable for parenteral administration conveniently comprise a sterile aqueous preparation of the active compound which is preferably isotonic with the blood of the recipient. Thus, such formulations may conveniently contain distilled water, 5% dextrose in distilled water or saline. Useful formulations also comprise concentrated solutions or solids containing the compound of formula (I) which upon dilution with an appropriate solvent give a solution suitable for parental administration above.

Topical formulations include ointments, creams, gels and lotions which may be prepared by conventional methods known in the art of pharmacy. In addition to the ointment, cream gel, or lotion base and the active ingredient, such topical formulation may also contain preservatives, perfumes, and additional active pharmaceutical agents.

In addition to the aforementioned ingredients, the formulations of this invention may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

EXAMPLES

The following examples illustrate aspects of this invention but should not be construed as limitations. The symbols and conventions used in these examples are consistent with those used in the contemporary chemical literature, for example, the *Journal of the American Chemical Society.*

Example 1

17β-N-1-(4-Chlorophenyl)cyclopentylcarbamoyl-4-aza-5α-androstan-3-one (Compound 1)

A. 17β-N-1-(4-Chlorophenyl)cyclopentylcarbamoyl-androst-4-en-3-one

To a suspension of 3-oxo-4-androstene-17β-carboxylic acid (Rasmusson, G. H. et al., *J. Med. Chem.*, 27, 1690 (1984)) (10.44 g, 32.9 mmol), in toluene (330 mL) and dry pyridine (3.75 ml) at 0° C. is added thionyl chloride (3.6 mL, 49 mmol). The reaction mixture is stirred at 0° C. for 15 min and then stirred at room temperature for 1 h. The reaction mixture is then cooled to 0° C., treated with 4-N,N-dimethylaminopyridine (1.01 g, 8.28 mmol) and 1-amino-1-(4-chlorophenyl)cyclopentane (12.90 g, 65.9 mmol; prepared by Curtius rearrangement of the corresponding acid) and allowed to warm to room temperature and stir overnight. Next the reaction is extracted sequentially with 1N HCl, 10% NaOH, water and brine, dried over sodium sulfate, and filtered. The filtrate is concentrated and flash chromatographed on silica gel, eluting with a 35–50% ethyl acetate-hexane gradient to give, after concentration, 17β-N-1-(4-chlorophenyl)cyclopentylcarbamoyl-androst-4-en-3-one as an off-white foam; yield: 8.44 g (52%).

B. 17β-N-1-(4-Chlorophenyl)cyclopentylcarbamoyl-5-oxo-A-nor-3,5-secoandrostan-3-oic acid To a refluxing solution of 17β-N-1-(4-chlorophenyl)cyclopentylcarbamoylandrost-4-en-3-one (8.44 g, 17.1 mmol) prepared in part A above, t-butanol (130 mL), sodium carbonate (3.18 g, 25.6 mmol), and water (35 mL) is added, over 35 min, a 75° C. solution of potassium permanganate (0.67 g, 4.3 mmol), sodium periodate (25.57 g , 120 mmol) and water (190 mL). After refuxing an additional 25 min, the heterogeneous mixture is cooled to room temperature, filtered through a bed of celite, the solid is washed with water and the filtrate concentrated in vacuo to remove t-butanol. The resulting aqueous solution is acidified to pH 2 with 6N HCl and then extracted with $CH_2Cl_2$ (4×100 mL). The $CH_2Cl_2$ layers are combined and washed with water, dried over sodium sulfate, filtered and concentrated in vacuo to give 17β-N-1-(4-chlorophenyl)cyclopentylcarbamoyl-5-oxo-A-nor-3,5-secoandrostan-3-oic acid as a off-white solid; yield: 7.30 g (83% crude). This material is carried directly into step C below.

C. 17β-N-1-(4-Chlorophenyl)cyclopentylcarbamoyl-4-aza-androst-5-en-3-one

To a suspension of 17β-N-1-(4-chlorophenyl)cyclopentylcarbamoyl-5-oxo-A-nor-3,5-secoandrostan-3-oic acid (4.78 g, 9.30 mmol), from step B, in dry ethylene glycol (20 mL) at −5° C. is added ammonia (ca. 3.5 mL, 0.14 mol) and the mixture stirred at 0° C. for 30 min. The resulting solution is heated to 170° C. over 1 h, and after 1 h at 170° C., the reaction mixture is cooled to 30° C. and water is added. The resulting slurry is diluted with 1N HCl, extracted with chloroform (4×100 mL), the extracts dried over sodium sulfate, filtered and concentrated to give 17β-N-1-(4-chlorophenyl)cyclopentylcarbamoyl-4-aza-androst-5-en-3-one as a tan solid; yield: 5.08 g (100% crude). This material is carried directly into step D below.

D. 17β-N-1-(4-Chlorophenyl)cyclopentylcarbamoyl-4-aza-5α-androstan-3-one

To a solution of 17β-N-1-(4-chlorophenyl)cyclopentylcarbamoyl-4-aza-androst-5-en-3-one (from above, ca. 9.30 mmol) in acetic acid (120 mL) is added platinum oxide (0.32 g). The resultant mixture is charged to 56 psi with hydrogen and heated at 75° C. for 5 h then allowed to cool to room temperature overnight. After replacing the hydrogen atmosphere with nitrogen, the reaction mixture is filtered through celite and the celite pad washed with $CH_2Cl_2$. Toluene is added and the filtrate is concentrated in vacuo to an oil which is purified by flash chromatography (toluene/acetone/ethyl acetate, 6:3:1 to 1:3:1) to give 17β-N-1-(4-chlorophenyl)cyclopentylcarbamoyl-4-aza-5α-androstan-3-one as a mixture with the corresponding 17β primary amide; yield: 0.69 g, (15%). Subsequent purification of this material by HPLC (BDS Hypersil C8 column, 50% $CH_3CN$/water) and trituration with hot ethyl acetate gave a pure sample: m.p. 261–263° C.; Anal. Calcd. for $C_{30}H_{41}ClN_2O_2 \cdot \frac{1}{4}H_2O$: C, 71.83; H, 8.34; N, 5.58. Found: C, 71.85; H 8.23; N, 5.59.

Example 2

17β-N-1-(4-Chlorophenyl)cyclopentylcarbamoyl-4-methyl-4-aza-5α-androstan-3-one (Compound 2)

Starting with 17β-N-1-(4-chlorophenyl)cyclopentylcarbamoyl-5-oxo-A-nor-3,5-secoandrostan-3-oic acid (1.73 g, 3.36 mmol), from example 1, step B, and following the procedures of example 1, step C and D, with the substitution of methylamine for ammonia in step C, 17β-N-1-(4-chlorophenyl)cyclopentylcarbamoyl-4-methyl-4-aza-5α-androstan-3-one is prepared, m.p. 125–130° C. Anal. Calcd. for $C_{31}H_{43}ClN_2O_2 \cdot \frac{1}{2}H_2O$: C, 71.37; H, 8.38; N, 5.31. Found: C, 71.58; H, 8.53; N, 5.39.

Example 3

17β-N-1-(4-Chlorophenyl)cyclopentylcarbamoyl-4-aza-5α-androst-1-en-3-one (Compound 3)

To a suspension of 3-oxo-4-aza-5α-androst-1-ene-17β-carboxylic acid (Rasmusson, G. H. et al, *J. Med. Chem.,* 29, 2298 (1986)) (0.159 g, 0.50 mmol), in toluene (5 ml), dimethylformamide (0.5 mL), and pyridine (0.06 mL, 0.7 mmol) at 0° C. is added thionyl chloride (0.05 mL, 0.7 mmol). After 15 min the ice bath is removed and the reaction mixture allowed to warm to room temperature. After 1 h, the reaction mixture is concentrated in vacuo. The residue is dissolved in dry $CH_2Cl_2$ and 1-amino-1-(4-chlorophenyl)cyclopentane (0.49 g, 2.5 mmol; prepared by Curtius rearrangement of the corresponding acid) is added at room temperature followed by 4-N,N-dimethylaminopyridine (0.061 g, 0.50 mmol). After 4 h, 1 N HCl is added, the mixture extracted with $CHCl_3$ (3×100 mL), the $CHCl_3$ dried over $MgSO_4$, filtered and concentrated. The residue is flash chromatographed on silica gel (toluene/acetone/ethyl acetate, 26:3:1 to 11:3:1) to give a white solid on concentration. This material is triturated with ethyl acetate to give 17β-N-1-(4-chlorophenyl)cyclopentylcarbamoyl-4-aza-5α-androst-1-en-3-one as a white solid; yield: 129 mg, (52%); m.p. 307–309° C. (decomp.). Anal. Calcd. for $C_{30}H_{39}ClN_2O_2$: C, 72.78; H, 7.94; N, 5.66. Found: C, 72.59; H, 7.93; N, 5.54.

Examples 4–21

These compounds were prepared as outlined in example 3 above. Amines of formula (IIa) which were not commercially available were prepared as described.

Example 4

17β-N-1-(4-t-Butylphenyl)cyclopentylcarbamoyl-4-aza-5α-androst-1-en-3-one (Compound 4)

Melting Point: 282–285° C.

Anal. Calcd. for $C_{34}H_{48}N_2O_2 \cdot \frac{1}{4}H_2O$: C, 78.34; H, 9.38; N, 5.37. Found: C, 78.29; H, 9.40; N, 5.38.

Example 5

17β-N-1-(4-t-Butylphenyl)cyclohexylcarbamoyl-4-aza-5α-androst-1-en-3-one (Compound 5)

Melting Point: 233–236° C.

Anal. Calcd. for $C_{35}H_{50}N_2O_2 \cdot \frac{1}{2}H_2O$: C, 77.88; H, 9.52; N, 5.19. Found: C, 77.82; H, 9.54; N, 5.21.

Example 6

17β-N-1-(4-Chlorophenyl)cyclohexylcarbamoyl-4-aza-5α-androst-1-en-3-one (Compound 6)

Melting Point: 270–272° C.

Anal. Calcd. for $C_{31}H_{47}ClN_2O_2$: C, 73.13; H, 8.12; N, 5.50. Found: C, 73.06; H, 8.14; N, 5.47.

Example 7

17β-N-1-(4-Trifluoromethylphenyl)cyclopentylcarbamoyl-4-aza-5α-androst-1-en-3-one (Compound 7)

Melting Point: 294–297° C.

Anal. Calcd. for $C_{31}H_{39}F_3N_2O_2$: C, 70.43; H, 7.44; N, 5.30. Found: C, 70.34; H, 7.46; N, 5.23.

Example 8

17β-N-1-(4-Methoxyphenyl)cyclopentylcarbamoyl-4-aza-5α-androst-1-en-3-one (Compound 8)

Melting Point: 257–260° C.
Anal. Calcd. for $C_{31}H_{42}N_2O_3$: C, 75.88; H, 8.63; N, 5.71. Found: C, 75.86; H, 8.57; N, 5.60.

Example 9

17β-N-1-(4-Fluorophenyl)cyclopentylcarbamoyl-4-aza-5α-androst-1-en-3-one (Compound 9)

Melting Point: 290° C.
Anal. Calcd. for $C_{30}H_{39}FN_2O_2$: C, 75.28; H, 8.21; N, 5.85. Found: C, 75.09; H, 8.26; N, 5.75.

Example 10

17β-N-1-(4-Fluorophenyl)cyclohexylcarbamoyl-4-aza-5α-androst-1-en-3-one (Compound 10)

Melting Point: 283–285° C.
Anal. Calcd. for $C_{31}H_{41}FN_2O_2$: C, 75.58; H, 8.39; N, 5.69. Found: C, 75.63; H, 8.45; N, 5.67.

Example 11

17β-N-1-(4-Methoxyphenyl)cyclohexylcarbamoyl-4-aza-5α-androst-1-en-3-one (Compound 11)

Melting Point: 238–240° C.
Anal. Calcd. for $C_{32}H_{44}N_2O_3 \cdot \frac{1}{4}H_2O$: C, 75.48; H, 8.81; N, 5.50. Found: C, 75.42; H, 8.78; N, 5.51.

Example 12

17β-N-1-(3,4-Methylenedioxyphenyl)cyclohexylcarbamoyl-4-aza-5α-androst-1-en-3-one (Compound 12)

Melting Point: 255–257° C.
Anal. Calcd. for $C_{32}H_{42}N_2O_4$: C, 74.10; H, 8.16; N, 5.40. Found: C, 74.07; H, 8.17; N, 5.37.

Example 13

17β-N-1-(4-t-Butylphenyl)cycloheptylcarbamoyl-4-aza-5α-androst-1-en-3-one (Compound 13)

Melting Point: 152–162° C.
Anal. Calcd. for $C_{36}H_{52}N_2O_2 \cdot \frac{1}{2}H_2O$: C, 78.07; H, 9.65; N, 5.06. Found: C, 78.11; H, 9.64; N, 5.04.

Example 14

17β-N-4-(4-t-Butylphenyl)tetrahydropyranylcarbamoyl-4-aza-5α-androst-1-en-3-one (Compound 14)

Melting Point: 240–242° C.
HRMS Calcd. for $C_{34}H_{48}N_2O_3$: 533.375143. Found: 533.37512 (−1.5 ppm).

Example 15

17β-N-1-(2,4-Dichlorophenyl)cyclopropylcarbamoyl-4-aza-5α-androst-1-en-3-one (Compound 15)

Melting Point: 297–298° C.
Anal. Calcd. for $C_{28}H_{34}Cl_2N_2O_2$: C, 67.06; H, 6.83; N, 5.59. Found: C, 67.18; H, 6.86; N, 5.53.

Example 16

17β-N-1-(4-Trifluoromethylphenyl)-2,2-diethylcyclopropylcarbamoyl-4-aza-5α-androst-1-en-3-one (Compound 16)

Melting Point: 225–228° C.
Anal. Calcd. for $C_{33}H_{43}F_3N_2O_2$: C, 71.20; H, 7.79; N, 5.03. Found: C, 70.92; H, 7.77; N, 4.99.

Example 17

17β-N-1-(4-t-Butylphenyl)-4,4-dimethylcyclohexylcarbamoyl-4-aza-5α-androst-1-en-3-one (Compound 171)

Melting Point: 172–175° C.
Anal. Calcd. for $C_{37}H_{54}N_2O_2 \cdot \frac{1}{3}H_2O$: C, 78.68; H, 9.76; N, 4.96. Found: C, 78.58; H, 9.69; N, 4.74.

Example 18

17β-N-1-(4-t-Butylphenyl)-4-t-Butylcyclohexylcarbamoyl-4-aza-5α-androst-1-en-3-one (Compound 18)

Melting Point: 189–194° C.
Anal. Calcd. for $C_{39}H_{58}N_2O_2$: C, 79.81; H, 9.96; N, 4.77. Found: C, 79.65; H, 9.89; N, 4.75.

Example 19

17β-N-1-(3-Trifluoromethylphenyl)cyclopentylcarbamoyl-4-aza-5α-androst-1-en-3-one (Compound 19)

Melting Point: 258–260° C.
Anal. Calcd. for $C_{31}H_{39}F_3N_2O_2$: C, 70.43; H, 7.44; N, 5.30. Found: C, 70.35; H, 7.39; N, 5.30.

Example 20

17β-N-4-(4-t-Butylphenyl)tetrahydrothiopyranylcarbamoyl-4-aza-5α-androst-1-en-3-one (Compound 20)

Melting Point: 267–268° C.
Anal. Calcd. for $C_{34}H_{48}N_2O_2S \cdot H_2O$: C, 72.04; H, 8.89; N, 4.94. Found: C, 72.19; H, 8.54; N, 4.92.

Example 21

17β-N-1-(4-Biphenyl)-2,2-diethylcycloprooylcarbamoyl-4-aza-5α-androst-1-en-3-one (Compound 21)

Melting Point: 167–174° C.
Anal. Calcd. for $C_{38}H_{48}N_2O_2 \cdot \frac{1}{2}H_2O$: C, 79.54; H, 8.61; N, 4.88. Found: C, 79.34; H, 8.43; N, 4.76.

Example 22

17β-N-(2,5-bis(Trifluoromethyl))phenylcarbamoyl-4-aza-5α-androstan-3-one (Compound 22)

A. 17β-N-(2,5-bis(Trifluoromethyl))phenylcarbamoyl-androst-4-en-3-one

To a solution of 3-oxo-4-androstene-17β-carboxylic acid (Rasmusson, G. H. et al., *J. Med. Chem.*, 27, 1690 (1984))

(17.2 g, 54.4 mmol), dry THF (180 mL) and dry pyridine (7 ml) at 2° C. is added thionyl chloride (5.1 mL, 70.8 mmol). The reaction mixture is stirred at 2° C. for 20 min and then stirred at room temperature for 40 min. The reaction mixture is then filtered and the solid washed with toluene. The filtrate is concentrated in vacuo to an oil which is diluted with dry THF (150 mL) and dry pyridine (7 mL). To the resultant dark solution is added 2,5-bis(trifluoromethyl)aniline (9.4 mL, 59.8 mmol) and the reaction mixture is refluxed for 5 h, diluted with methylene chloride, extracted sequentially with 1N HCl and brine, dried over sodium sulfate, and filtered. The filtrate is concentrated and applied to a column of 500 g of silica gel and the column eluted with a 15–30% ethyl acetate-hexane gradient to give, after concentration, 17β-N-(2,5-bis(trifluoromethyl))phenylcarbamoyl-androst-4-en-3-one as an off-white foam; yield: 18.3 g (64%).

B. 17β-N-(2,5-bis(Trifluoromethyl))phenylcarbamoyl-5-oxo-A-nor-3,5-secoandrostan-3-oic acid To a refluxing solution of 17β-N-(2,5-bis (trifluoromethyl))phenylcarbamoyl-androst-4-en-3-one (18.3 g, 34.9 mmol) prepared in part A above, t-butanol (275 mL), sodium carbonate (6.3 g, 50.8 mmol), and water (36 mL) is added, over 45 min, a 75° C. solution of potassium permanganate (0.38 g, 2.4 mmol), sodium periodate (52.2 g , 245 mmol) and water (311 mL). After refuxing an additional 15 min, the heterogeneous mixture is cooled to room temperature and celite (50 g) is added. The reaction mixture is filtered through a bed of celite (50 g) and the solid is washed with water and the filtrate concentrated in vacuo to remove t-butanol (ca. 175 ml). The resultant aqueous solution is acidified to pH 2 with 36% HCl and the extracted 4 times with chloroform. The chloroform layers are combined and washed with water, brine, dried over sodium sulfate, filtered and concentrated in vacuo to give 17β-N-(2,5-bis (trifluoromethyl))phenylcarbamoyl-5-oxo-A-nor-3,5-secoandrostan-3-oic acid as a off-white solid; yield: 20.5 g (100% crude). This material is carried directly into step C below.

C. 17β-N-(2,5-bis(Trifluoromethyl))phenylcarbamoyl-4-aza-androst-5-en-3-one

To a suspension of 17β-N-(2,5-bis(trifluoromethyl)) phenylcarbamoyl-5-oxo-A-nor-3,5-secoandrostan-3-oic acid (20.5 g, 34.8 mmol), from step B, in dry ethylene glycol (100 mL) at room temperature is added ammonia (ca. 8 mL, 0.32 mol) over a 5 min period. The resultant solution is heated to 180° C. over 45 min, and after 12 min at 180° C., the reaction mixture is cooled to 70° C. and water (116 mL) is added over a period of 5 min. The resultant suspension is cooled to 7° C. and stirred for 10 min and filtered under vacuum. The solid is washed with water (60 mL) and then is dissolved in chloroform and washed with water, brine, dried over sodium sulfate, filtered and concentrated. The residue is dissolved in chloroform and applied to a column of 110 g of silica gel and the column eluted with a 2–5% isopropanol-chloroform gradient to give 17β-N-(2,5-bis (trifluoromethyl))phenylcarbamoyl-4-aza-androst-5-en-3-one as an off-white solid; yield: 16.5 g (90%).

D. 17β-N-(2,5-bis(Trifluoromethyl))phenylcarbamoyl-4-aza-5α-androstan-3-one

To a solution of 17β-N-(2,5-bis(trifluoromethyl)) phenylcarbamoyl-4-aza-androst-5-en-3-one (8.9 g, 16.7 mmol) in acetic acid (120 mL) is added platinum oxide (0.9 g). The resultant mixture is charged to 50 psi with hydrogen and heated at 60–70° C. for 6 h. After replacing the hydrogen atmosphere with nitrogen, the reaction mixture is filtered through celite and the celite pad washed with acetic acid (30 mL), chloroform (60 mL) and toluene (200 mL). The filtrate is concentrated in vacuo to an oil, toluene (200 mL) is added and the solution concentrated to a foam in vacuo. The foam is crystallized from ethyl acetate-heptane to give, after drying in vacuo at 85° C. for 1 h, 17β-N-(2,5-bis (trifluoromethyl))phenylcarbamoyl-4-aza-5α-androstan-3-one; yield: 4.78 g, (54%); m.p. 245–247° C. Anal. Calcd. for $C_{27}H_{32}F_6N_2O_2$: C, 61.12; H, 6.08; N, 5.28. Found: C, 61.13; H, 6.12; N, 5.21.

Example 23

17β-N-(2,5-bis(Trifluoromethyl))phenylcarbamoyl-4-methyl-4-aza-5α-androstan-3-one (Compound 23)

A. 17β-N-(2,5-bis(Trifluoromethyl))phenylcarbamoyl-4-methyl-4-aza-androst-5-en-3-one To a suspension of 17β-N-(2,5-bis(trifluoromethyl)) phenylcarbamoyl-5-oxo-A-nor-3,5-secoandrostan-3-oic acid (1.7 g, 3.1 mmol), from example 1—step B, in dry ethylene glycol (8.5 mL) at room temperature is added methylamine (ca. 1 mL, 22.5 mmol) and the resultant solution is heated to 180° C. over 1 h. After 15 min at 180° C., the reaction mixture is cooled to room temperature and water (10 mL) is added. The reaction mixture is stirred at 7° C. for 10 min and is filtered under vacuum. The solid is washed with water (5 mL) and is subsequently dissolved in chloroform and washed with water, brine, dried over sodium sulfate, filtered and concentrated. The residue is applied to a column of 110 g of silica gel and the column eluted with a 2–5% methanol-methylene chloride gradient to give 17β-N-(2,5-bis(trifluoromethyl))-phenylcarbamoyl-4-methyl-4-aza-androst-5-en-3-one as an off-white foam; yield: 1.11 g (66%).

B. 17β-N-(2,5-bis(Trifluoromethyl)phenylcarbamoyl-4-methyl-4-aza-5α-androstan-3-one To a solution of 17β-N-(2,5-bis(trifluoromethyl)) phenylcarbamoyl-4-methyl-4-aza-androst-5-en-3-one (1.0 g, 1.9 mmol) in acetic acid (10 mL) is added platinum oxide (0.10 9). The resultant mixture is charged to 50 psi with hydrogen and is heated at 60–70° C. for 45 min. After replacing the hydrogen atmosphere with nitrogen, the reaction mixture is filtered through celite and the celite pad washed with acetic acid (10 mL), chloroform (60 mL) and toluene (30 mL). The filtrate is concentrated in vacuo to an oil, toluene (30 mL) is added, and the solution concentrated to a foam in vacuo. This material is chromatographed twice on 93 g of silica gel by eluting with a 2 to 4% gradient of methanol-methylene chloride to give, after drying in vacuo at 60° C. for 21 h, 17β-N-(2,5-bis(trifluoromethyl)) phenylcarbamoyl-4-methyl-4-aza-5α-androstan-3-one, m.p. 103–105° C. Anal. Calcd. for $C_{28}H_{34}F_6N_2O_2$: C, 61.76; H, 6.29; N, 5.14. Found: C, 61.60; H, 6.32; N, 5.08.

Example 24

17β-N-(2-t-Butyl-5-trifluoromethyl) phenylcarbamoyl-4-aza-5α-androst-1-en-3-one (Compound 24)

To a suspension of 3-oxo-4-aza-5α-androst-1-ene-17β-carboxylic acid (Rasmusson, G. H. et al., *J. Med. Chem.,* 29, 2298 (1986)) (0.021 g, 0.063 mmol), dry methylene chloride (6 ml) and dry pyridine (8.1 mL, 0.1 mmol) at 0° C. is added thionyl chloride (6.8 mL, 0.095 mmol). The ice bath is removed and the reaction mixture allowed to warm to room temperature. After 1 h, toluene (1 mL) is added and the reaction mixture is concentrated in vacuo. The residue is dissolved in dry methylene chloride (1.5 mL) and dry pyridine (8.5 mL, 0.11 mmol) and 2-t-butyl-5- trifluoromethylaniline (0.023 g, 0.126 mmol ) is added at room temperature. After 13 h, methylene chloride (20 mL) is added and the reaction mixture is washed with 1M sulfuric acid, saturated sodium bicarbonate solution, brine, dried over sodium sulfate, filtered and concentrated in vacuo. The residue is chromatographed on 7 g of silica gel by eluting with a 2.5 to 5% methanol-methylene chloride gradient to give 0.01 g of a white foam. This material is crystallized from ethyl acetate-hexanes to give 17β-N-(2-t-Butyl-5-trifluoromethyl)phenylcarbamoyl-4-aza-5α-androst-1-en-3-one as a white solid; m.p. 263–264° C. Mass Spectrum (m/z)=517 MH+

Example 25

17β-N-(2-t-Butyl-5-trifluoromethyl) phenylcarbamoyl-4-aza-5α-androstan-3-one (Compound 25)

Compound 25 is prepared as described for Example 1 using a corresponding amount of 2-t-butyl-5-trifluoromethylaniline in place of 1-amino-1-(4-chlorophenyl)cyclopentane.

Melting Point: 256–259° C.

Anal. Calcd. for $C_{30}H_{41}F_3N_2O_2$: C, 69.47; H, 7.97; N, 5.40. Found: C, 69.49; H, 8.00; N, 5.41.

Example 26

17β-N-(2-t-Butyl-5-trifluoromethyl) phenylcarbamoyl-4-methyl-4-aza-5α-androstan-3-one (Compound 26)

Compound 26 is prepared by a method analogous to that of Example 2.

Melting Point: 229–232° C.

Anal. Calcd. for $C_{31}H_{43}F_3N_2O_2$: C, 69.90; H, 8.14; N, 5.26. Found: C, 69.79; H, 8.07; N, 5.19.

Example 27

17β-N-(2,5-Di-t-butyl)phenylcarbamoyl-4-aza-5α-androst-1-en-3-one (Compound 27)

Compound 27 is prepared by a method analogous to that of Example 3.

Melting Point: 165–171° C. (dec.)

Anal. Calcd. for $C_{33}H_{48}N_2O_2 \cdot \frac{2}{3}H_2O$: C, 76.70; H, 9.62; N, 5.42. Found: C, 76.76; H, 9.51; N, 5.43.

Example 28

17β-N-(2,5-Di-t-butyl)phenylcarbamoyl-4-aza-5α-androstan-3-one (Compound 28)

Compound 28 is prepared as described for Example 1 using a corresponding amount of 2,5-di-t-butylaniline in place of 1-amino-1-(chlorophenyl)cyclopentane.

Melting Point: 162–164° C.

Anal. Calcd. for $C_{33}H_{50}N_2O_2 \cdot \frac{1}{4}H_2O$: C, 77.52; H, 9.96; N, 5.48. Found: C, 77.58; H, 9.97; N, 5.48.

Example 29

17β-N-(2,5-Di-t-butyl)phenylcarbamoyl-4-methyl-4-aza-5α-androstan-3-one (Compound 29)

Compound 29 is prepared by a method analogous to that of Example 2.

Melting Point: 150–152° C.

Anal. Calcd. for $C_{34}H_{52}N_2O_2$: C, 78.41; H, 10.06; N, 5.38. Found: C, 78.17; H, 10.01; N, 5.33.

Example 30

17β-N-(2,5-bis(Trifluoromethyl)phenylcarbamoyl-4-aza-7β-methyl-5α-androst-1-en-3-one (Compound 30)

A. 3β-Triisopropylsilyloxyetienic acid methyl ester

A suspension of 3β-hydroxyetienic acid methyl ester (*J. Med. Chem.* 27, 1690) (516 g, 1.55 mol) in DMF (800 mL) is heated to 55° C., imidazole (264 g, 3.88 mol) added with vigorous mechanical stirring, followed by dropwise addition of triisopropylsilylchloride (360 g, 1.87 mol). The reaction becomes homogeneous after about half of the triisopropylsilylchloride is added and the reaction temperature increases to ca. 70° C. The reaction is complete by TLC (35% ethyl acetate/hexanes) after 1.5 hrs and a thick slurry forms. The reaction is cooled to 0° C., 1 L of ice water added with stirring, the solid collected by filtration and washed with water (500 mL) and methanol (500 mL). The resulting tan solid is suspended in methanol (1 L) and allowed to stir overnight to give, on filtration, 3β-triisopropylsilyloxyetienic acid methyl ester as a tan solid of sufficient purity to carry on to the following steps.

B. 3β-Triisopropylsilyloxy-7-oxo-etienic acid methyl ester

To a suspension of chromic acid (50.7 g, 507 mmol) in dichloromethane (175 ml) at 0° C. is added 3,5-dimethyl pyrazole (48.7 g, 507 mmol) and the reaction mixture is stirred 30 min. Next 3-β-triisopropylsilyloxyetienic acid methyl ester, as prepared in Part A, (31 g, 63.4 mmol) in dichloromethane (120 ml) is added and the reaction allowed to stir at ambient temperature for 21 h. An aqueous solution of NaOH (2N, 100 ml) is then added followed by celite (ca. 200 cc), the reaction is filtered through glass wool, the solvent removed in vacuo and the resulting residue partitioned between ethyl acetate:water. The organics are washed with 2N NaOH , water, saturated aqueous NaCl, and dried over $MgSO_4$ and the solvent is removed by rotary evaporation. The residue is flash chromatographed on silica gel (5–15% ethyl acetate/hexane) to give 3β-triisopropylsilyloxy-7-oxo-etienic acid methyl ester as a white solid; yield: 13.8 g, (43%); Anal. Calcd. for $C_{30}H_{50}O_4Si$: C, 71.66; H, 10.02. Found: C, 71.43; H, 10.10.

C. 3β-Triisopropylsilyloxy-7β-methyl etienic acid methyl ester

To a slurry of methyl triphenylphosphonium iodide (14 g, 34.6 mmol) in tetrahydrofuran (THF 60 ml) at 0° C. is added n-butyl lithium (21.7 ml, 1.6M in hexane, 34.7 mmol). After stirring 20 min a solution of 3β-triisopropylsilyloxy-7-oxo-etienic acid methyl ester (8.72 g, 17.3 mmol) in 25 ml THF is added. After 10 min water (120 ml) is added followed by saturated aqueous $NaHSO_4$ solution (15 ml). The product is then extracted with ethyl acetate (200 ml), dried over $MgSO_4$, concentrated to ca. 50 ml, treated with tris (triphenylphosphine)rhodium chloride (460 mg, 0.51 mmol) and stirred under a hydrogen atmosphere overnight. The catalyst is filtered through a plug of silica gel and the filtrate is condensed and flash chromatographed on silica gel (35% ethyl acetate/hexane) to give 3β-triisopropylsilyloxy-7β-methyl etienic acid methyl ester as a white foam; yield: 4.29 g of a 3:1 mixture of 7β:7α epimers (86%); Anal. Calcd. for $C_{31}H_{54}O_3Si$: C, 74.04; H, 10.82. Found: C, 74.15; H, 10.88.

D. 3β-Hydroxy-7β-methyl etienic acid methyl ester

To a solution of 3β-triisopropylsilyloxy-7β-methyl etienic acid methyl ester (4.25 g, 8.45 mmol) in 25 ml THF is added tetrabutylammonium fluoride (17 ml, 1M in THF, 17 mmol) followed by stirring 6 h at room temperature. Water (100 ml) and ethyl acetate (150 ml) are added and the organic phase is washed with water, saturated aqueous NaCl, dried over $MgSO_4$, and concentrated. The resulting concentrate is flash chromatographed on silica gel (25–40% ethyl acetate/hexane) to give 3β-hydroxy-7β-methyl etienic acid methyl ester; yield: 2.65 g, (90%); Anal. Calcd. for $C_{22}H_{34}O_3 \cdot \frac{1}{4}H_2O$: C, 75.28; H, 9.91. Found: C, 75.67; H, 9.98.

E. 17β-Carbomethoxy-7β-methyl-androst-4-en-3-one

To a solution of 3βhydroxy-7β-methyl etienic acid methyl ester (6.6 g, 19 mmol) in 220 ml acetone is added 7.5 ml Jones' reagent (3.1 M, 23.3 mmol) the reaction stirred 1 h and concentrated to ca. 40 ml. The resulting residue is taken up in ethyl acetate, washed with 2N NaOH, water, saturated aqueous NaCl, dried over $MgSO_4$, concentrated, and flash chromatographed on silica gel (35% ethyl acetate/hexane) to give 17β-carbomethoxy-7β-methyl-androst-4-en-3-one as a yellow oil; yield: 2.73 g, (42%); high resolution mass spectra Calcd. for $[MH+]C_{22}H_{33}O_3$: 345.2428, Found: 345.2430.

F. 17β-Carbomethoxy-7β-methyl-5-oxo-A-nor-3,5-secoandrostan-3-oic acid

To a solution of 17β-carbomethoxy-7β-methyl-androst-4-en-3-one (2.9 g, 8.4 mmol) in 60 ml tert-butanol is added sodium carbonate (1.04 g, 8.4 mmol) in 6 ml water, a slurry of sodium periodate (9 g, 42 mmol) and potassium permanganate (134 mg, 850 mmol) in ca. 35 ml water and the reaction heated at reflux for 48 h. After cooling to room temperature the solids are removed by filtration, washed with water and concentrated to leave an aqueous residue which is acidified with saturated aqueous $NaHSO_4$, extracted with ethyl acetate, washed with water, saturated aqueous NaCl, dried over $MgSO_4$, concentrated, and flash chromatographed on silica gel (5–10% methanol/dichloromethane) to give 17β-carbomethoxy-7β-methyl-5-oxo-A-nor-3,5-secoandrostan-3-oic acid; yield: 1.2 g, (39%); high resolution mass spectra Calcd. for $[MH+]C_{21}H_{33}O_5$: 365.2328, Found: 365.2328.

G. 17β-Carbomethoxy-7β-methyl-4-aza-androst-5-en-3-one

To a suspension of 17β-carbomethoxy-7β-methyl-5-oxo-A-nor-3,5-secoandrostan-3oic acid (1.2 g, 3.29 mmol) in 8 ml anhydrous ethylene glycol is added ammonia (ca. 15 ml, 4.2 mmol) at −40° C., the mixture stirred 30 min and then heated to 170° C. for 45 min. The reaction mixture is then cooled to room temperature and water is added. The resulting slurry is extracted with ethyl acetate, the extracts washed with saturated aqueous NaCl, dried over $MgSO_4$, and concentrated. The resulting concentrate is flash chromatographed on silica gel (3–5% methanol/dichloromethane) to give 17β-carbomethoxy-7β-methyl-4-aza-androst-5-en-3-one; yield: 590 mg, (52%); Anal. Calcd. for $C_{21}H_{31}NO_3$: C, 73.01; H; 9.04; N, 4.05; Found: C, 72.97; H, 8.98; N, 4.04.

H. 17β-Carbomethoxy-7β-methyl-4-aza-5α-androstan-3-one

To a solution of 17β-carbomethoxy-7β-methyl-4-aza-androst-5-en-3-one (590 mg, 1.71 mmol) in 20 ml acetic acid is added platinum oxide (60 mg, 0.26 mmol). The resulting mixture is charged to 40 psi with hydrogen, shaken 16 h, and purged with nitrogen. The catalyst is filtered, and the filtrate condensed. The resulting oil is flash chromatographed on silica gel (3–5% methanol/dichloromethane) to give 17β-carbomethoxy-7β-methyl-4-aza-5α-androstan-3-one; yield: 465 mg, (78%); high resolution mass spectra Calcd. for $[MH+]C_{21}H_{34}NO_3$: 348.2539, Found: 348.2537.

I. 17β-Carbomethoxy-7β-methyl-4-aza-5α-androst-1-en-3-one

To a solution of 17β-carbomethoxy-7β-methyl-4-aza-5α-androstan-3-one (182 mg, 0.52 mmol) in 4 ml dioxane is added 2,3-dichloro-5,6-dicyanobenzoquinone (120 mg, 0.52 mmol), bis(trimethylsilyl)trifluoroacetamide (0.56 ml, 2.1 mmol) and the mixture stirred at room temperature overnight. The reaction is condensed and the resulting oil taken up in dichloromethane (75 ml) and washed with 2N NaOH, water, saturated aqueous NaCl, dried over $MgSO_4$, and concentrated. The resulting concentrate is flash chromatographed on silica gel (50% ethyl acetate/hexane) to give 17β-carbomethoxy-7β-methyl-4-aza-5α-androst-1-en-3-one as a tan foam; yield: 150 mg, (83%); high resolution mass spectra Calcd. for $[MH+]C_{21}H_{32}NO_3$: 346.2382, Found: 346.2382.

J. 3-Oxo-4-aza-7β-methyl-5α-androst-1-en-17β-carboxylic acid

To a suspension of 17β-carbomethoxy-7β-methyl-4-aza-5α-androst-1-en-3-one (180 mg, 0.52 mmol) in 5 ml dioxane at 55° C. is added lithium hydroxide (43 mg, 1.02 mmol) in water (2 ml) and the reaction stirred 24 overnight. Water is added (25 ml) followed by saturated aqueous $NaHSO_4$, extraction with ethyl acetate, subsequent washing with saturated aqueous NaCl, drying over $MgSO_4$, and concentration to a residue which is flash chromatographed on silica gel (50% ethyl acetate/hexane) to give a white solid; yield: 94 mg, (55%); high resolution mass spectra Calcd. for $[MH+]C_{20}H_{30}NO_3$: 332.2225, Found: 332.2226.

K. 17β-N-(2,5-bis(Trifluoromethyl))phenylcarbamoyl-4-aza-7β-methyl-5α-androst-1-en-3-one To a suspension of 3-Oxo-4-aza-7β-methyl-5α-androst-1-en-17β-carboxylic acid (50 mg, 0.15 mmol) in 1.5 ml 0.03% DMF in toluene at 0° C. is added pyridine (0.030 ml, 0.37 mmol) and thionyl chloride (0.013 ml, 0.18 mmol). After 15 min, the reaction mixture is warmed to room temperature for 1.5 h, excess reagents are removed via azeotrope and the resulting solids slurried in 1.5 ml toluene. The reaction mixture is treated with 4-(N,N-dimethylamino) pyridine (1 mg, cat.), heated to 100° C. and 2,5-bis(trifluoromethyl)aniline (0.035 ml, 0.22 mmol) is added. After 3.5 h the reaction is condensed, partitioned with ethyl acetate/saturated aqueous $NaHSO_4$, and the organic phase is washed with 2N NaOH, saturated aqueous NaCl, dried over $MgSO_4$, and condensed. The concentrate is purified via flash chromatography (10% ethyl acetate/dichloromethane) followed by HPLC (BDS Hypersil C8 column, 40–70% $CH_3CN$/water), and lyophilization to give a white solid; yield: 12 mg, (15%); high resolution mass spectra Calcd. for $[MH+]C_{28}H_{33}F_6N_2O_2$: 543.2456, Found: 543.2446.

Example 31

7β-N-(2-t-Butyl-5-trifluoromethyl)phenylcarbamoyl-4-aza-7β-methyl-5α-androst-1-en-3-one (Compound 31)

To a suspension of 3-oxo-4-aza-7β-methyl-5α-androst-1-en-17β-carboxylic acid, as prepared in Part J of Example 31, (38 mg, 0.12 mmol) in 1.5 ml 0.03% DMF in toluene at 0° C. is added pyridine (0.023 ml, 0.29 mmol) and thionyl chloride (0.010 ml, 0.14 mmol). After 15 min, the reaction mixture is warmed to room temperature for 1.5 h, excess reagents are removed via azeotrope and the resulting solids dissolved in dichloromethane (1 ml), treated with pyridine (0.025 ml, 0.30 mmol), and 2-t-butyl-5-trifluoromethylaniline (50 mg, 0.23 mmol). After 24 h the reaction mixture is diluted with dichloromethane (20 ml), washed with saturated aqueous $NaHSO_4$, 2N NaOH, saturated aqueous NaCl, dried over $MgSO_4$, condensed, and purified via flash chromatography on silica gel (40% ethyl acetate/hexane); yield: 15 mg, (25%); high resolution mass spectra Calcd. for $[MH+]C_{31}H_{42}F_3N_2O_2$: 531.3198, Found: 531.3206.

Example 32
17β-N-1-(4-Chlorophenyl)cyclopentylcarbamoyl-4-aza-7β-methyl-5α-androst-1-en-3-one (Compound 32)

This compound is prepared by the procedure of Example 3 except a corresponding amount of 3-Oxo-4-aza-7β-methyl-5α-androst-1-en-17β-carboxylic acid, as prepared in Part J of Example 31, is used in place of 3-oxo-4-aza-5α-androst-1-ene-17β-carboxylic acid. High resolution mass spectra Calcd. for [MH+]$C_{31}H_{42}ClN_2O_2$: 509.2931, Found: 509.2935.

Example 33
17β-N-9-(4-t-Butylphenyl)bicyclo[3.3.1]nonylcarbamoyl-4-aza-5α-androst-1-en-3-one (Compound 33)

Compound 33 is prepared in an analogous manner as in Example 3 using 9-amino-bicyclo[3.3.1]nonane in place of 1-amino-1-(4-chlorophenyl)cyclopentane to give 17β-N-9-(4-t-butylphenyl)bicyclo[3.3.1 ]nonylcarbamoyl-4-aza-5α-androst-1-en-3-one as a white solid; m.p. 277–280° C. Anal. Calcd. for C38H$_{54}$N$_2$O$_2$.½H$_2$O: C, 78.71; H, 9.56; N, 4.83. Found: C, 78.92; H, 9.50; N, 4.81.

Examples 34–57
These compounds may be prepared as outlined in Example 3. Amines which were not commercially available were prepared as described in WO94/14833.
34. 17β-N-(5-Chloro-2-t-butyl)phenylcarbamoyl-4-aza-5α-androst-1-en-3-one
35. 17β-N-(4-Bromo-2-t-butyl)phenylcarbamoyl-4-aza-5α-androst-1-en-3-one
36. 17β-N-(2-t-Butyl-5-phenyl)phenylcarbamoyl-4-aza-5α-androst-1-en-3-one
37. 17β-N-(4-t-Butyl-2-trifluoromethyl)phenylcarbamoyl-4-aza-5α-androst-1-en-3-one
38. 17β-N-(2-Phenyl-5-trifluoromethyl)phenylcarbamoyl-4-aza-5α-androst-1-en-3-one
39. 17β-N-(2-t-Butyl-5-(4-chlorophenyl))phenylcarbamoyl-4-aza-5α-androst-1-en-3-one
40. 17β-N-(2-(4-t-Butyl)phenyl-5-trifluoromethyl)phenylcarbamoyl-4-aza-5α-androst-1-en-3-one
41. 17β-N-(2-t-Butyl-5-(4-t-butyl)phenyl)phenylcarbamoyl-4-aza-5α-androst-1-en-3-one
42. 17β-N-(4-Chloro-2,5-bis(trifluoromethyl))phenylcarbamoyl-4-aza-5α-androst-1-en-3-one
43. 17β-N-(2-(2,4-Dichlorophenyl)-5-trifluoromethyl)phenylcarbamoyl-4-aza-5α-androst-1-en-3-one
44. 17β-N-(4-Bromo-2-trifluoromethyl)phenylcarbamoyl-4-aza-5α-androst-1-en-3-one
45. 17β-N-(5-Bromo-2-trifluoromethyl)phenylcarbamoyl-4-aza-5α-androst-1-en-3-one
46. 17β-N-(4,5-Dibromo-2-trifluoromethyl)phenylcarbamoyl-4-aza-5α-androst-1-en-3-one
47. 17β-N-(5-t-Butyl-4-chloro-2-trifluoromethyl)phenylcarbamoyl-4-aza-5α-androst-1-en-3-one
48. 17β-N-(5-t-Butyl-6-chloro-2-trifluoromethyl)phenylcarbamoyl-4-aza-5α-androst-1-en-3-one
49. 17β-N-(2,4-Bis(trifluoromethyl))phenylcarbamoyl-4-aza-5α-androst-1-en-3-one
50. 17β-N-(2-t-Butyl-4-trifluoromethyl)phenylcarbamoyl-4-aza-5α-androst-1-en-3-one
51. 17β-N-1-(4-t-Butyl-2-trifluoromethylphenyl)cyclopentylcarbamoyl-4-aza-5α-androst-1-en-3-one
52. 17β-N-1-(4-Cyanophenyl)cyclohexylcarbamoyl-4-aza-5α-androst-1-en-3-one
53. 17β-N-1-(3-(3-Fluorophenyl)phenyl)cyclopentylcarbamoyl-4-aza-5α-androst-1-en-3-one
54. 17β-N-1-(5-Indanyl)cyclohexylcarbamoyl-4-aza-5α-androst-1-en-3-one
55. 17β-N-1-(5-Chloro-2,4-dimethylphenyl)cyclopentylcarbamoyl-4-aza-5α-androst-1-en-3-one
56. 17β-N-2-(4-trifluoromethylphenyl)bicyclo[3.2.1]octanylcarbamoyl-4-aza-5α-androst-1-en-3-one.
57. 17β-N-(5-Bromo-2-t-butyl)phenylcarbamoyl-4-aza-5α-androst-1-en-3-one

Example 58
Pharmaceutical formulations
(A) Transdermal System—For 1000 Patches

| Ingredients | Amount |
| --- | --- |
| Active compound | 40 g |
| Silicone fluid | 450 g |
| Colloidal silicon dioxide | 25 g |

The silicone fluid and active compound are mixed together and the colloidal silicone dioxide is added to increase viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene, polyvinyl acetate or polyurethane), and an impermeable backing membrane made of a polyester multilaminate. The resulting laminated sheet is then cut into 10 sq. cm patches.

(B) Oral Tablet—For 1000 Tablets

| Ingredients | Amount |
| --- | --- |
| Active compound | 20 g |
| Starch | 20 g |
| Magnesium Stearate | 1 g |

The active compound and the starch are granulated with water and dried. Magnesium stearate is added to the dried granules and the mixture is thoroughly blended. The blended mixture is compressed into tablets.

(C) Suppository—For 1000 Suppositories

| Ingredients | Amount |
| --- | --- |
| Active compound | 25 g |
| Theobromine sodium salicylate | 250 g |
| Witepsol S55 | 1725 g |

The inactive ingredients are mixed and melted. The active compound is then distributed in the molten mixture, poured into molds and allowed to cool.

(D) Injection—For 1000 Ampules

| Ingredients | Amount |
| --- | --- |
| Active Compound | 5 g |
| Buffering Agents | q.s. |
| Propylene glycol | 400 mg |
| Water for injection | 600 mL |

The active compound and buffering agents are dissolved in the propylene glycol at about 50° C. The water for injection is then added with stirring and the resulting solution is filtered, filled into ampules, sealed and sterilized by autoclaving.

(E) Capsule—For 1000 Capsules

| Ingredients | Amount |
|---|---|
| Active Compound | 20 g |
| Lactose | 450 g |
| Magnesium stearate | 5 g |

The finely ground active compound is mixed with the lactose and stearate and packed into gelatin capsules.

We claim:

1. A compound of formula (I)

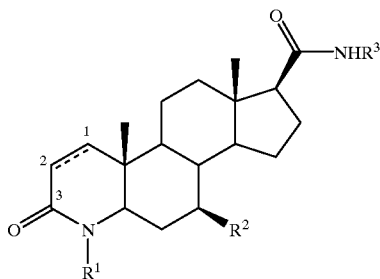

(I)

wherein carbons 1 and 2 are joined by either a single or a double bond;
$R^1$ is hydrogen or methyl;
$R^2$ is hydrogen or methyl;
$R^3$ is (B)

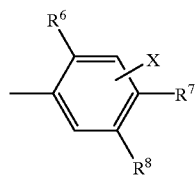

(B)

wherein $R^6$ is trifluoromethyl, phenyl optionally substituted with one or more halogens or branched ($C_{4-7}$) alkyl groups, or branched ($C_{4-7}$) alkyl;
either of $R^7$ or $R^8$ is trifluoromethyl, halogen, phenyl optionally substituted with one or more halogens or branched ($C_{4-7}$)alkyl groups, or branched ($C_{4-7}$)alkyl, while the other is hydrogen or halogen; and
X is hydrogen or halogen,
or a pharmaceutically acceptable solvate thereof.

2. A compound as claimed in claim 1 wherein X is hydrogen.

3. A compound as claimed in claim 1 wherein $R^2$ is hydrogen.

4. A compound as claimed in claim 1 wherein $R^6$ is trifluoromethyl, phenyl optionally substituted with one or more halogens, or branched ($C_{4-7}$) alkyl; and either of $R^7$ or $R^8$ is trifluoromethyl, halogen, phenyl optionally substituted with one or more halogens, or branched ($C_{4-7}$) alkyl, while the other is hydrogen or halogen.

5. A compound as claimed in claim 1 wherein carbons 1 and 2 are joined by a double bond.

6. A compound as claimed in claim 1 of formula (IB);

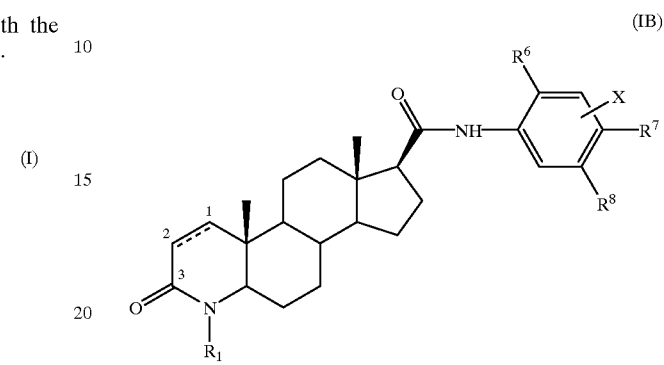

(IB)

wherein carbons 1 and 2 are joined by either a single or a double bond;
$R^1$ is hydrogen or methyl;
$R^6$ is trifluoromethyl, phenyl optionally substituted with one or more halogens, or branched ($C_{4-7}$) alkyl;
either of $R^7$ or $R^8$ is trifluoromethyl, halogen, phenyl optionally substituted with one or more halogens, or branched ($C_{4-7}$) alkyl, while the other is hydrogen or halogen; and
X is hydrogen or halogen.

7. A compound as claimed in claim 6 wherein when $R^7$ or $R^8$ is branched ($C_{4-7}$) alkyl and X is hydrogen, $R^6$ is trifluoromethyl or phenyl optionally substituted with one or more halogens.

8. A compound as claimed in claim 6 wherein $R^6$ is trifluoromethyl or branched ($C_{4-7}$) alkyl; and either of $R^7$ or $R^8$ is trifluoromethyl, halogen, or phenyl substituted with one or more halogens, while the other is hydrogen or halogen.

9. A compound as claimed in claim 8 wherein $R^6$ is trifluoromethyl or branched ($C_{4-7}$) alkyl; either of $R^7$ or $R^8$ is trifluoromethyl while the other is hydrogen; and X is hydrogen.

10. A compound as claimed in claim 6 wherein $R^6$ and $R^8$ are independently trifluoromethyl or t-butyl, while $R^7$ and X are hydrogen.

11. A pharmaceutical formulation comprising an effective amount of a compound as claimed in claim 1 a pharmaceutically acceptable carrier thereof.

12. A process for preparing a compound as claimed in claim 1 which comprises:

(A) for compounds of formula (I) wherein carbons 1 and 2 are joined by a single bond, hydrogenating a compound of formula (IVa)

(IVa)

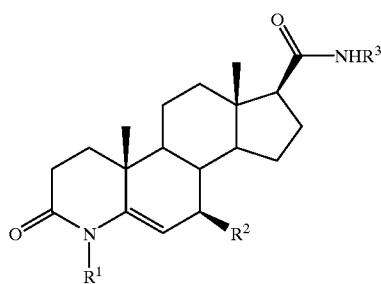

(B) for compounds of formula (I) wherein carbons 1 and 2 are joined by a double bond, reacting a compound of formula (V)

(V)

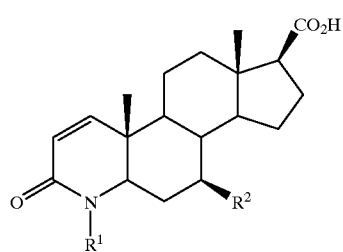

with a compound of formula (IIa)

 (IIa)

and if necessary and/or desired, subjecting the compound thus obtained to one or more further reactions comprising:

(i) interconversion to another compound of formula (I);

(ii) removing any protecting group or groups; and/or (iii) converting the compound of formula (I) or a solvate thereof into a pharmaceutically acceptable solvate thereof.

13. A process as claimed in claim 12 wherein in process (B) the compound of formula (V) is treated with a halogenating agent in the presence of a base prior to reaction with a compound of formula (IIa).

14. A process as claimed in claim 12 wherein in step (i) a compound of formula (I) wherein there is a double bond between carbons 1 and 2 and wherein $R^2$ is hydrogen is prepared by dehydrogenating a compound of formula (Ia).

(Ia)

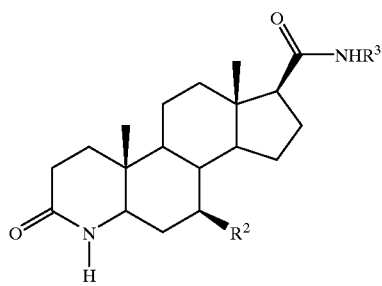

15. A method of inhibiting 5α-testosterone reductase enzyme comprising contacting said enzyme with an effective 5α-testosterone inhibitory amount of a compound as claimed in claim 1.

16. A method of treating an androgen responsive or mediated disease in a mammal suffering from said disease comprising administering to said mammal, an effective androgen responsive or mediated disease amount of a compound as claimed in claim 1.

17. A method of claim 16 wherein the androgen responsive or mediated disease is benign prostatic hyperplasia, prostate cancer, acne, male pattern baldness and hirsutism.

18. A compound of formula (IVa)

(IVa)

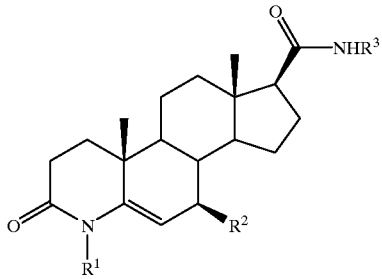

wherein $R^1$ and $R^2$ are independently hydrogen or methyl and $R^3$ is as defined in claim 1, or a solvate thereof.

19. The compound of claim 1 wherein said compound is selected from the group consisting of: 17β-N-(2,5-bis(Trifluoromethyl))phenylcarbamoyl-4-aza-5α-androstan-3-one, 17β-N-(2,5-bis(Trifluoromethyl))phenylcarbamoyl-4-methyl-4-aza-5α-androstan-3-one, 17β-N-(2-t-Butyl-5-trifluoromethyl)phenylcarbamoyl-4-aza-5α-androst-1-en-3-one, 17β-N-(2-t-Butyl-5-trifluoromethyl)phenylcarbamoyl-4-aza-5α-androstan-3-one, 17β-N-(2-t-Butyl-5-trifluoromethyl)phenylcarbamoyl-4-methyl-4-aza-5α-androstan-3-one, 17β-N-(2,5-Di-t-butyl)phenylcarbamoyl-4-aza-5α-androst-1-en-3-one, 17β-N-(2,5-Di-t-butyl)phenylcarbamoyl-4-aza-5α-androstan-3-one, 17β-N-(2,5-Di-t-butyl)phenylcarbamoyl-4-methyl-4-aza-5α-androstan-3-one, 17β-N-(2,5-bis(Trifluoromethyl)phenylcarbamoyl-4-aza-7β-methyl-5α-androst-1-en-3-one, and 17β-N-(2-t-Butyl-5-trifluoromethyl)phenylcarbamoyl-4-aza-7β-methyl-5α-androst-1-en-3-one.

* * * * *